US010475183B2

(12) United States Patent
Kawaguchi et al.

(10) Patent No.: US 10,475,183 B2
(45) Date of Patent: Nov. 12, 2019

(54) IMAGE ANALYSIS DEVICE, IMAGE ANALYSIS METHOD, IMAGE ANALYSIS SYSTEM, AND RECORDING MEDIUM

(71) Applicant: OSAKA UNIVERSITY, Suita-shi (JP)

(72) Inventors: Naomasa Kawaguchi, Suita (JP); Kazuaki Nakane, Suita (JP); Akihiro Takiyama, Sapporo (JP)

(73) Assignee: OSAKA UNIVERSITY, Suita-shi (JP)

( * ) Notice: Subject to any disclaimer, the term of this patent is extended or adjusted under 35 U.S.C. 154(b) by 154 days.

(21) Appl. No.: 15/743,808

(22) PCT Filed: Jul. 7, 2016

(86) PCT No.: PCT/JP2016/070143
§ 371 (c)(1),
(2) Date: Jan. 11, 2018

(87) PCT Pub. No.: WO2017/010397
PCT Pub. Date: Jan. 19, 2017

(65) Prior Publication Data
US 2018/0204324 A1 Jul. 19, 2018

(30) Foreign Application Priority Data

Jul. 15, 2015 (JP) ................................ 2015-141673

(51) Int. Cl.
*G06T 7/00* (2017.01)
*G01N 21/17* (2006.01)
(Continued)

(52) U.S. Cl.
CPC ........... *G06T 7/0014* (2013.01); *G01N 21/17* (2013.01); *G01N 21/84* (2013.01); *G01N 33/48* (2013.01);
(Continued)

(58) Field of Classification Search
CPC ........ G01N 21/17; G01N 21/84; G01N 33/48; G01N 33/483; G01N 33/4833; G06T 1/00;
(Continued)

(56) References Cited

U.S. PATENT DOCUMENTS 7,991,221 B1 * 8/2011 Kling .................. G06K 9/6252
382/154
8,718,377 B2 * 5/2014 Suzuki ................. G06T 7/0012
382/192

(Continued)

FOREIGN PATENT DOCUMENTS

EP 2383569 A1 2/2011
JP 201165253 A 3/2011
(Continued)

OTHER PUBLICATIONS

Kazuaki Nakane et al., "Image Diagnosis for Large Intestinal Cancer by Use of Algorithm. Employing Combinatorial Logic Invariants", roceedings of JAMIT Annual Meeting 2010, pp. 16 (Year: 2010).*

(Continued)

*Primary Examiner* — Mekonen T Bekele
(74) *Attorney, Agent, or Firm* — Kagan Binder, PLLC

(57) ABSTRACT

A relationship between constituents of a structure is objectively and appropriately assessed. An image analyzing device includes: a Betti number calculating section (42) configured to calculate the numbers of holes from respective plurality of binarized images, after the plurality of binarized images are generated by binarizing a single captured image, which is obtained by capturing a structure, while making binarization reference values differ from each other; a function specifying section (43) configured to specify a characteristic numerical value that characterizes a correspondence between (i) the respective binarization reference values and (Continued)

(ii) the respective numbers of holes; and an output information generating section (44) configured to generate output information corresponding to the characteristic numerical value.

10 Claims, 12 Drawing Sheets

(51) Int. Cl.
| | | |
|---|---|---|
| *G01N 33/48* | (2006.01) | |
| *G01N 33/483* | (2006.01) | |
| *G06T 1/00* | (2006.01) | |
| *G01N 21/84* | (2006.01) | |

(52) U.S. Cl.
CPC ....... *G01N 33/483* (2013.01); *G01N 33/4833* (2013.01); *G06T 1/00* (2013.01); *G06T 2207/10056* (2013.01); *G06T 2207/30024* (2013.01); *G06T 2207/30096* (2013.01)

(58) Field of Classification Search
CPC ......... G06T 7/0014; G06T 2207/10056; G06T 2207/30024; G06T 2207/30096; G06T 7/0012; G06T 7/12; G06T 7/187; G06T 7/62; G06K 9/00147
See application file for complete search history.

(56) References Cited

U.S. PATENT DOCUMENTS

| | | | | |
|---|---|---|---|---|
| 2008/0205764 | A1* | 8/2008 | Iwai | G06K 9/48 382/190 |
| 2010/0034439 | A1* | 2/2010 | Asano | G06T 15/08 382/128 |
| 2011/0274340 | A1* | 11/2011 | Suzuki | G06T 7/0012 382/133 |
| 2013/0163870 | A1 | 6/2013 | Cao et al. | |
| 2019/0012297 | A1* | 1/2019 | Kobayashi | G06F 17/16 |
| 2019/0180194 | A1* | 6/2019 | Kobayashi | G06N 20/00 |

FOREIGN PATENT DOCUMENTS

| | | |
|---|---|---|
| JP | 5522481 B2 | 4/2014 |
| WO | 2010087112 A1 | 8/2010 |

OTHER PUBLICATIONS

Nakane, Kazuaki et. Al., On the Classification of Colon Cancer Differentiation by Hierarchical Homology Sep. 10, 2015, 28, GO-14, pp. 1-3.

Nakane, Kazuaki et al., A simple mathematical model utilizing topological invariants for automatic detection of tumor areas in digital tissue images, Sep. 30, 2013, 8(Suppl 1): S27, pp. 1-4.

Nakane, Kazuaki et al., Homology-based method for detecting regions of interest and colonic digital images, Apr. 24, 2015, 10:36, pp. 1-5.

International preliminary report on patentability of PCT/JP2016/070143, 6 pages, dated Jan. 25, 2018.

International Search Report for PCT/JP2016/070143, 2 pages, dated Sep. 6, 2016.

Adcock, Aaron et al., Classification of Hepatic Lesions using the Matching Metric, Computer Vision and Image Understanding, vol. 121, p. 36-42, Oct. 3, 2012.

Extended European Search Report for Application No. 16824377.2, 5 pages, dated Apr. 18, 2018.

\* cited by examiner

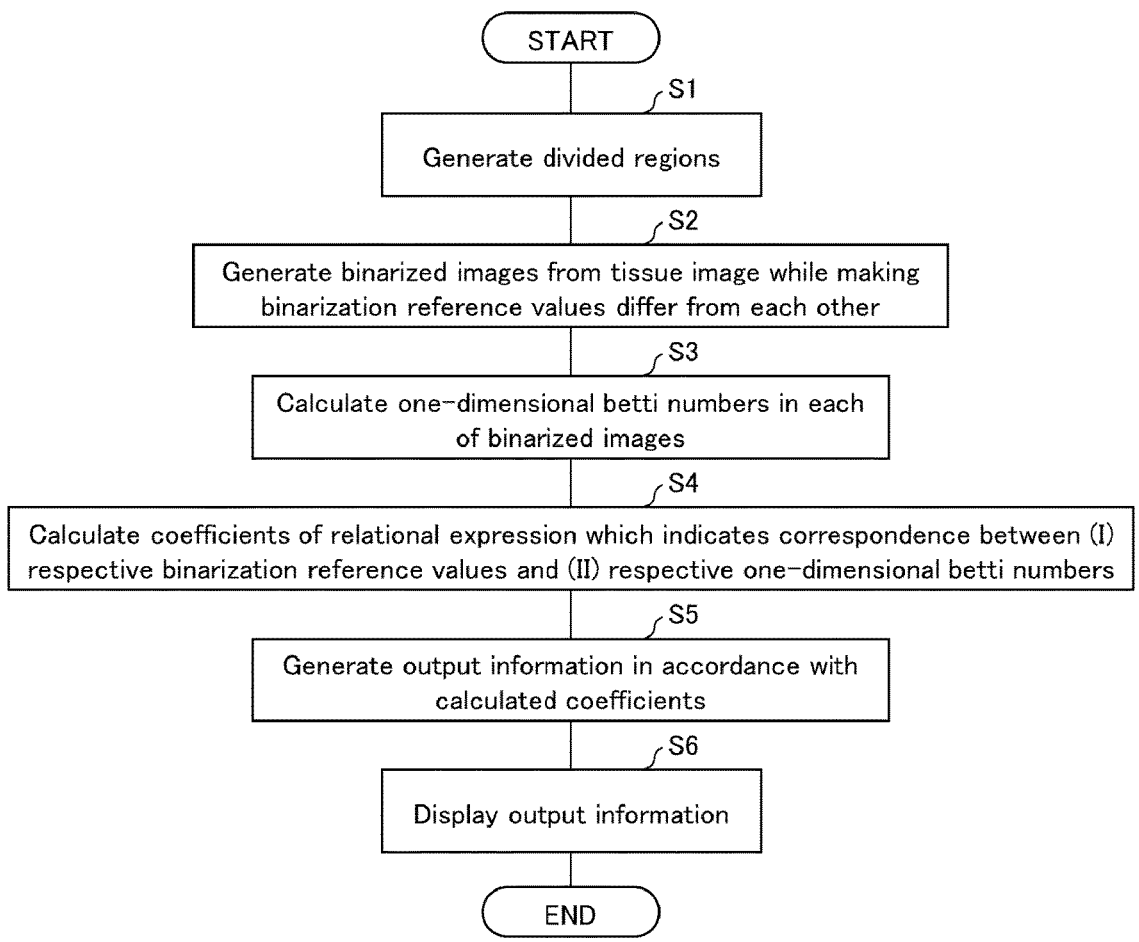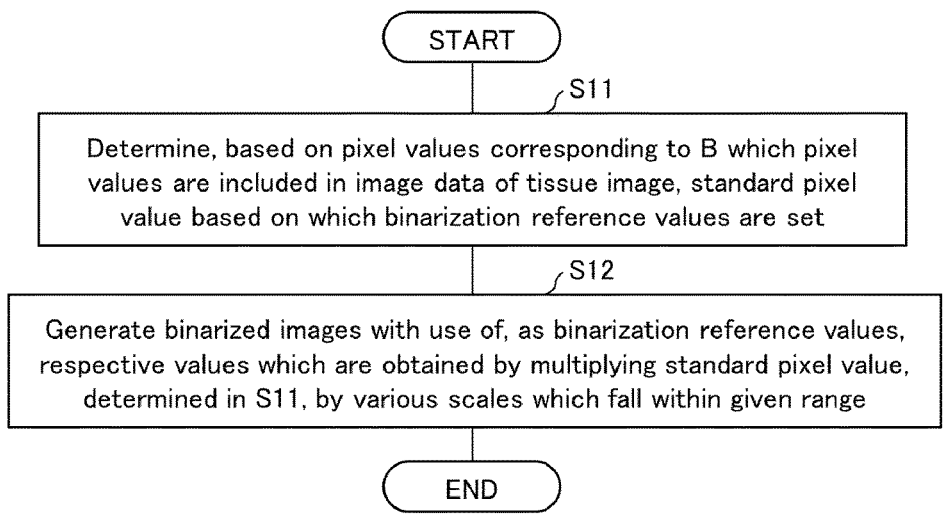

IMAGE ANALYSIS DEVICE, IMAGE ANALYSIS METHOD, IMAGE ANALYSIS SYSTEM, AND RECORDING MEDIUM

CROSS-REFERENCE TO RELATED APPLICATIONS

This application claims priority to International Application No. PCT/JP2016/070143, filed Jul. 7, 2016, and titled "IMAGE ANALYSIS DEVICE, IMAGE ANALYSIS METHOD, IMAGE ANALYSIS SYSTEM, IMAGE ANALYSIS PROGRAM, AND RECORDING MEDIUM", which in turn claims priority from Japanese Application having serial number 2015-141673, filed on Jul. 15, 2015, both of which are incorporated herein by reference in their entireties.

TECHNICAL FIELD

The present invention relates to an image analyzing device and an image analyzing method, each of which is for (i) analyzing an image which is obtained by capturing a structure and (ii) outputting information in accordance with which composition of the structure is determined.

BACKGROUND ART

A pathological diagnosis provides information important for determination of a treatment strategy. In a case where a pathological diagnosis is made, it is considered preferable to employ a double check system in order to avoid occurrence of a wrong diagnosis. This double check system is a system in which (i) a pathologist A makes a diagnosis, (ii) a pathologist B also makes a diagnosis, and then (iii) an outcome of a pathological diagnosis is determined based on findings which the respective pathologists A and B have obtained. However, under the circumstances, the absolute number of pathologists who make pathological diagnoses is insufficient, except for some of the developed countries. Moreover, such pathologists mostly work in hospitals in metropolitan areas and the like, and many hospitals do not have full-time pathologists. Therefore, not only in Japan but also in the world, it is not easy to always have a plurality of pathologists and let them promptly make pathological diagnoses. Furthermore, it is said that, in Japan, the average number of tissue slides which a pathologist observes so as to make pathological diagnoses is approximately 10,000 per year. As such, each pathologist has a heavy work load. In view of the circumstances, development of a technique has been desired which assists a pathologist in making a pathological diagnosis by causing a computer to take on a role of the pathologist in making the pathological diagnosis.

In a case where a pathologist makes a pathological diagnosis, the pathologist is required to make an objective determination on the basis of a morphological finding with regard to a tissue and/or cells which morphological finding is obtained by microscopic observation. However, some lesions are difficult to correctly classify and distinguish on the basis of merely morphological findings. Therefore, there is a possibility that a wrong pathological diagnosis, such an overlook of a lesion, is made. Furthermore, in a case where a pathologist makes a pathological diagnosis on the basis of subjective determination based on his/her experience, an outcome of the pathological diagnosis may vary depending on the pathologist. This causes a reduction in reliability of the pathological diagnosis. The technique which assists a pathologist in making a pathological diagnosis is required not to cause a wrong diagnosis, and is required to provide an objective criterion for a diagnosis.

In order that an image of, for example, a tissue slide used for a pathological diagnosis is analyzed with use of a computer, introduction of a topological idea has been suggested. As an example of the technique which assists a pathologist in making a pathological diagnosis, Patent Literature 1 discloses an image analyzing device which extracts a cancer lesion with reference to a pathological image. The image analyzing device disclosed in Patent Literature 1 calculates, for each region, homology per unit area of the pathological image, and then determines whether or not the each region is a target region (for example, a region including the cancer lesion).

Non-Patent Literature 1 discloses a method of analyzing an image of a liver under a concept of persistent homology and classifying a lesion in the liver.

CITATION LIST

Patent Literature

[Patent Literature 1]
WO2010/087112 (published on Aug. 5, 2010)

Non-Patent Literature

[Non-Patent Literature 1]
Aaron Adcock et al., "Classification of Hepatic Lesions using the Matching Metric", Computer Vision and Image Understanding, Vol. 121, p. 36-42, 2014.

SUMMARY OF INVENTION

Technical Problem

Appropriately evaluating a relationship between constituents of a structure is important in understanding a physical property and a configuration of the structure and determining composition of the structure.

To take, as an example, an image analysis which is effective in diagnosis of a cancer occurring in a tissue of a living body, as a cancer occurring in a tissue unusually grows, cells become deformed and intrinsic composition of the tissue is lost. This causes the tissue to be changed into a state where cancer cells are disorderly scattered. According to a pathological diagnosis, a "degree of differentiation" of a cancer is specified based on a pathologist's finding with regard to a morphology of a tissue and/or morphologies of cells.

According to the International Classification of Disease for Oncology, Third Revision (ICD-O-3), in a case where a large intestine cancer is represented as "(well, moderately, or poorly) differentiated" depending on a degree of differentiation of the large intestine cancer, the large intestine cancer is handled as an "adenocarcinoma" and is denoted by a morphology code "8140/3." Further, a "degree of differentiation" of a cancer (adenoma) is specified as follows. That is, in a case of, for example, an adenocarcinoma, a numeral 1, 2, or 3 each of which denotes a degree of differentiation is added to an end of the code 8140/3. Note that, as with the case of a conventional case, a degree of differentiation indicates a state where features of cells in a tissue are lost, in order of adenocarcinoma (moderately differentiated), and an adenocarcinoma (poorly differentiated).

Adenocarcinoma (well differentiated): 8140/31
Adenocarcinoma (moderately differentiated): 8140/32
Adenocarcinoma (poorly differentiated): 8140/33

A pathological diagnosis includes discriminating a degree of differentiation of a cancer. The fact that understanding a physical property and a configuration of a structure and determining composition of the structure is important is true not only for determining a cancer in a tissue of a living body but also for determining various structures.

The present invention has been made so as to solve the above problem, and an object of the present invention is to provide an image analyzing device and the like, each of which allows generation of information in accordance with which a relationship between constituents of a structure is appropriately assessed.

Solution to Problem

In order to attain the above object, an image analyzing device in accordance with an aspect of the present invention is an image analyzing device including: a binarizing section configured to generate a plurality of binarized images by binarizing, a plurality of times, a single captured image, which is obtained by capturing a structure, while making binarization reference values differ from each other; a space number calculating section configured to calculate the numbers of hole-shaped regions from the respective plurality of binarized images generated by the binarizing section; a specifying section configured to specify a characteristic numerical value that characterizes a correspondence between (i) the respective binarization reference values and (ii) the respective numbers of hole-shaped regions; and an output information generating section configured to generate output information corresponding to the characteristic numerical value specified by the specifying section.

In order to attain the above object, an image analyzing method in accordance with an aspect of the present invention is an image analyzing method for use in an image analyzing device that analyzes a single captured image which is obtained by capturing a structure, the method including the steps of: (a) generating a plurality of binarized images by binarizing, a plurality of times, the single captured image while making binarization reference values differ from each other; (b) calculating the numbers of hole-shaped regions from the respective plurality of binarized images generated in the step (a); (c) specifying a characteristic numerical value that characterizes a correspondence between (i) the respective binarization reference values and (ii) the respective numbers of hole-shaped regions; and (d) generating output information corresponding to the characteristic numerical value specified in the step (c).

Advantageous Effects of Invention

According to the present invention, it is possible to objectively and appropriately assess a variation in relationship between constituents of a structure by analyzing an image of the structure.

BRIEF DESCRIPTION OF DRAWINGS

FIG. 3 is a flowchart illustrating an example process flow carried out by an image analyzing device in accordance with Embodiment 1 of the present invention.

FIG. 4 is a flowchart illustrating an example process flow in which binarized images are generated by an image analyzing device in accordance with Embodiment 1 of the present invention.

Figure 5:
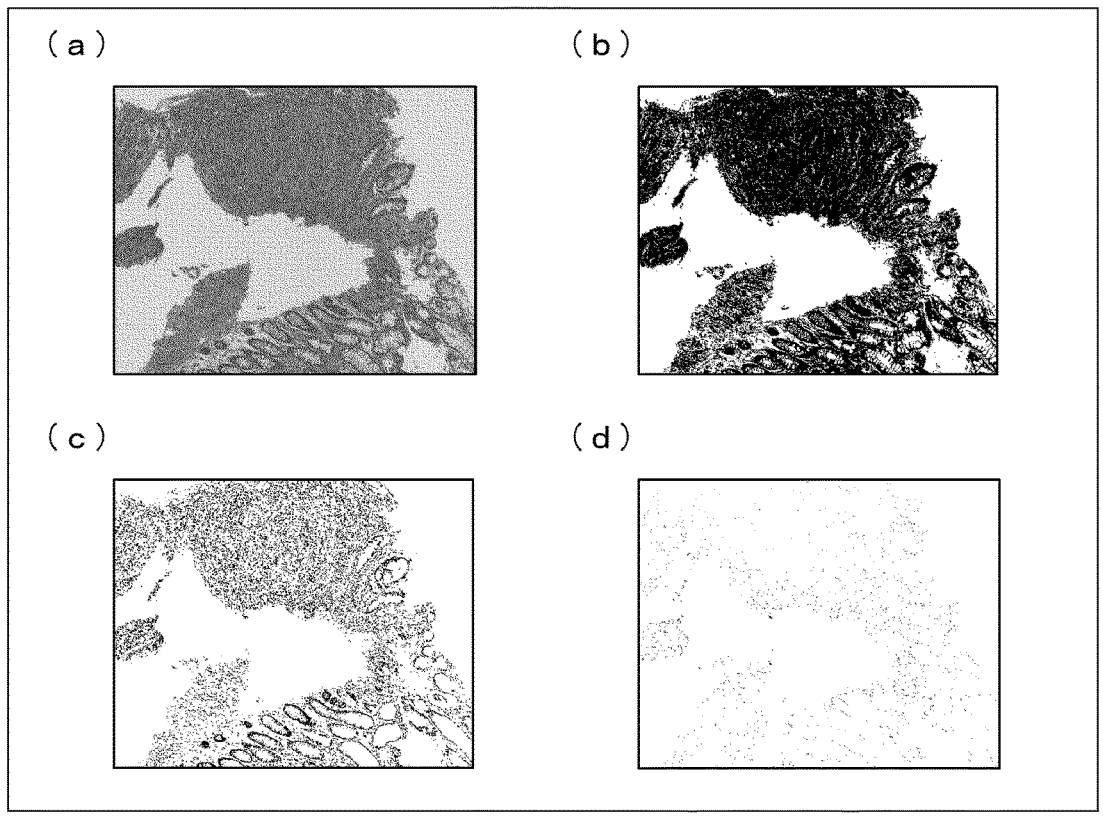

(a) of FIG. 5 is an original tissue image (the highest pixel value, corresponding to B, is 171). (b) of FIG. 5 is a view illustrating an example binarized image which is obtained by binarizing the original tissue image with use of a value obtained by multiplying, by 1 (one), the highest pixel value corresponding to B. (c) of FIG. 5 is a view illustrating an example binarized image which is obtained by binarizing the original tissue image with use of a value obtained by multiplying, by 0.7, the highest pixel value corresponding B. (d) of FIG. 5 is a view illustrating an example binarized image which is obtained by binarizing the original tissue image with use of a value obtained by multiplying, by 0.5, the highest pixel value corresponding to B.

Figure 6:
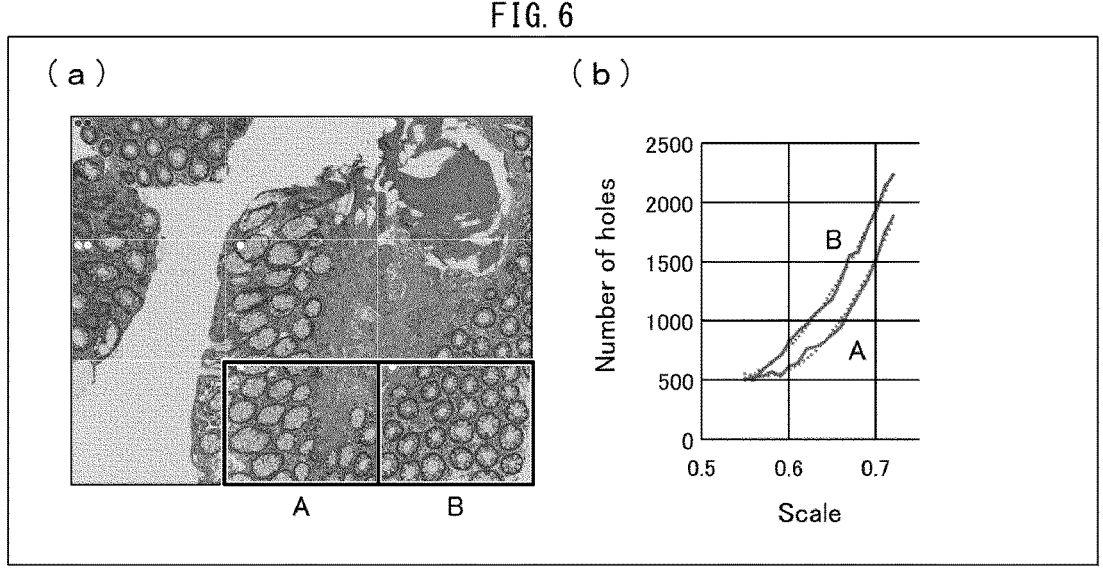

FIG. 6 is a view illustrating an example of a result of an analysis carried out with use of an image analyzing device.

Figure 7:
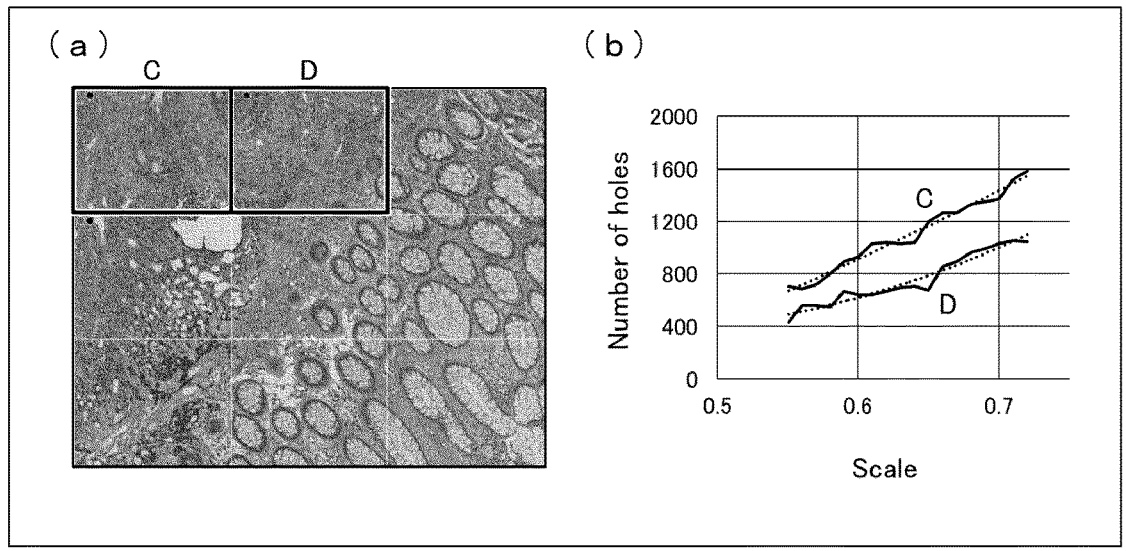

FIG. 7 is a view illustrating an example of a result of an analysis carried out with use of an image analyzing device.

Figure 8:
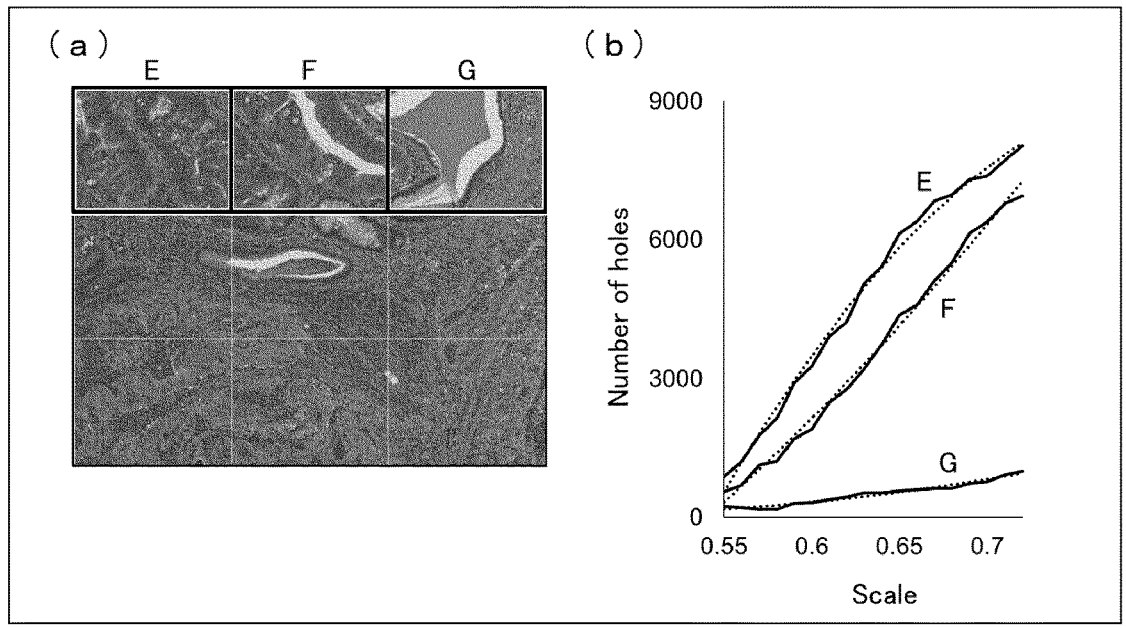

FIG. 8 is a view illustrating an example of a result of an analysis carried out with use of an image analyzing device.

Figure 9:
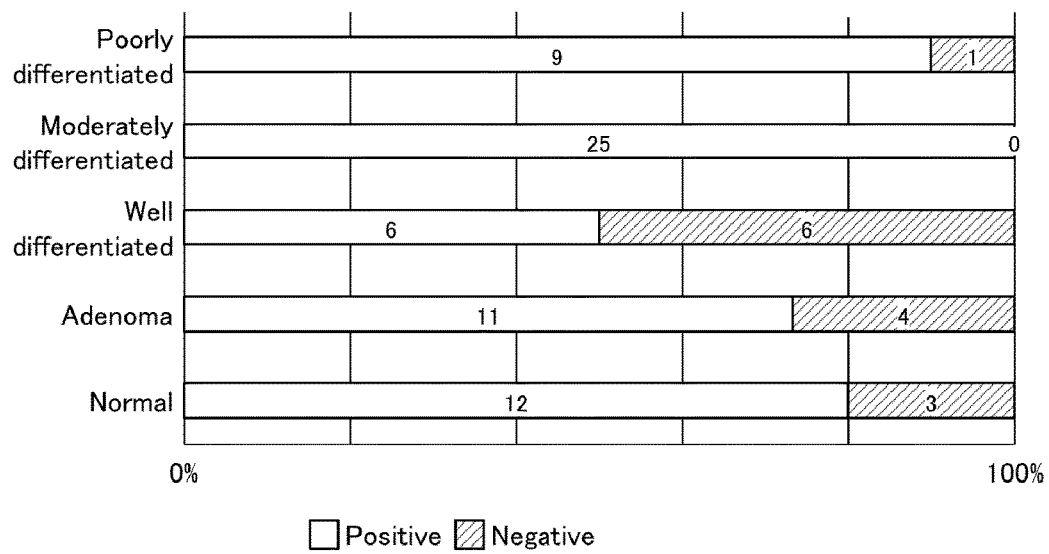

FIG. 9 is a graph illustrating ratios between (i) a case(s) where a quadratic coefficient "a" of an approximate expression was positive and (ii) a case(s) where a quadratic coefficient "a" of an approximate expression was negative.

Figure 10:
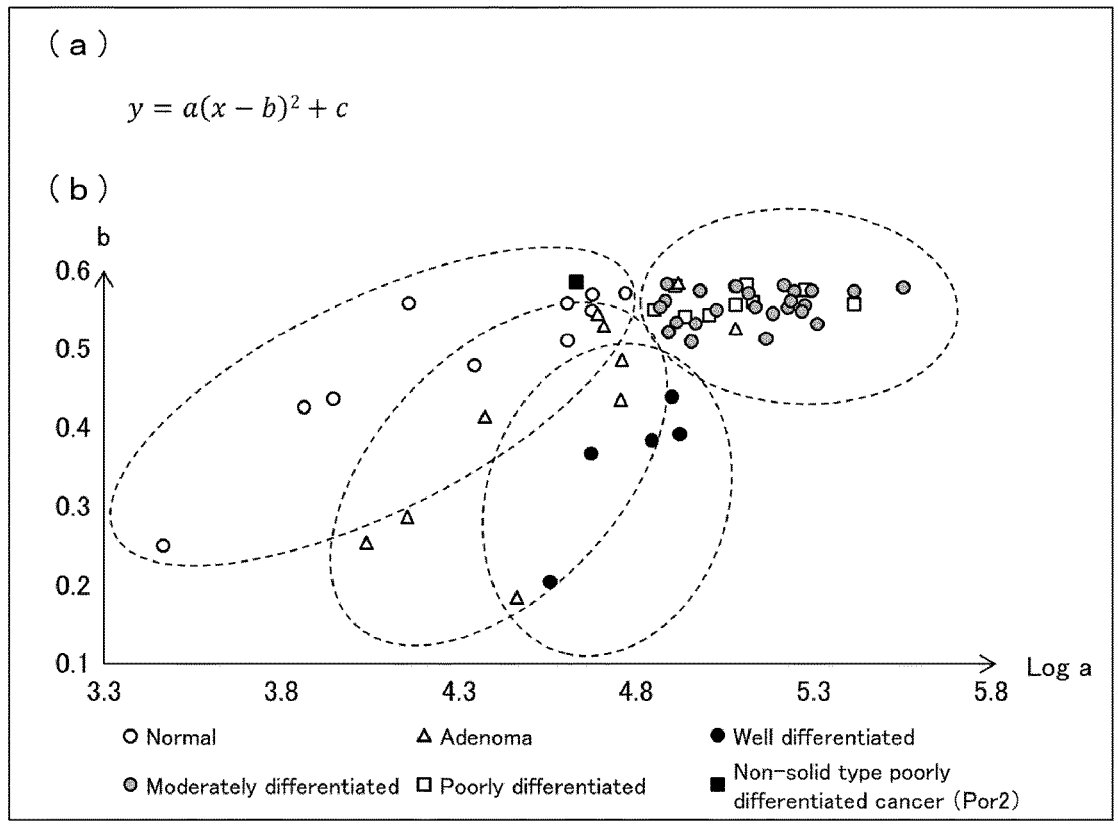

(a) of FIG. 10 illustrates an example of a quadratic function employed as an approximate expression. (b) of FIG. 10 is a distribution chart obtained by plotting a point having, as coordinates, (i) a logarithm of a quadratic coefficient of the approximate expression and (ii) "b" indicative of a position of an axis of the approximate expression.

Figure 11:
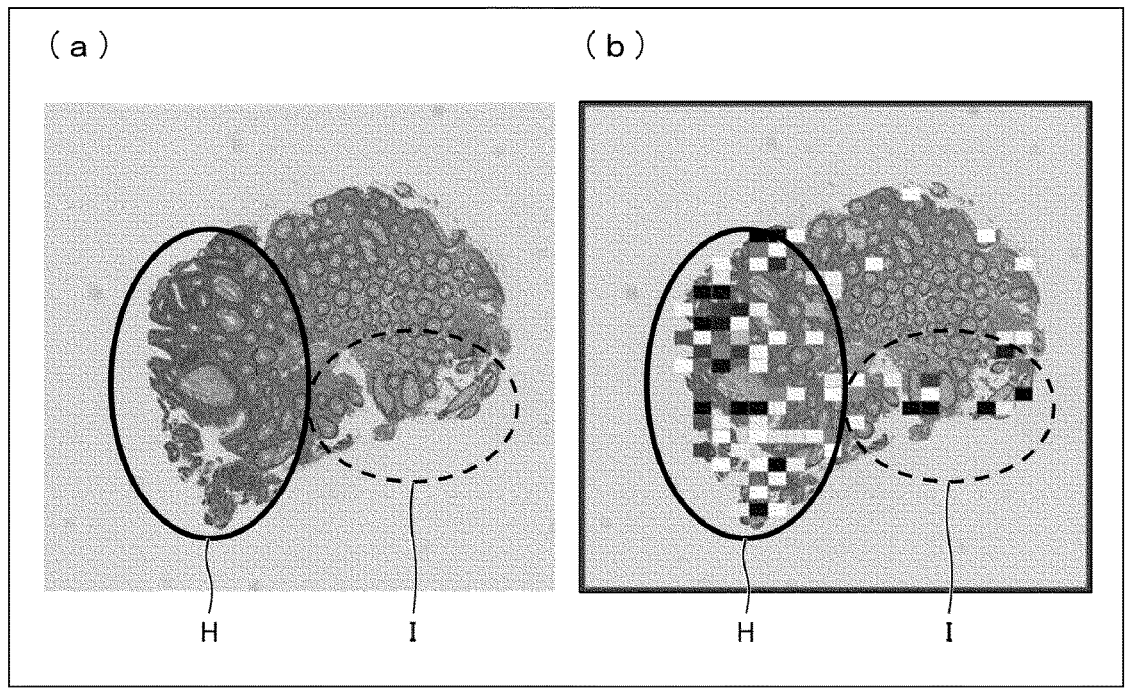

FIG. 11 is a view illustrating an example of a determination-purpose image.

Figure 12:
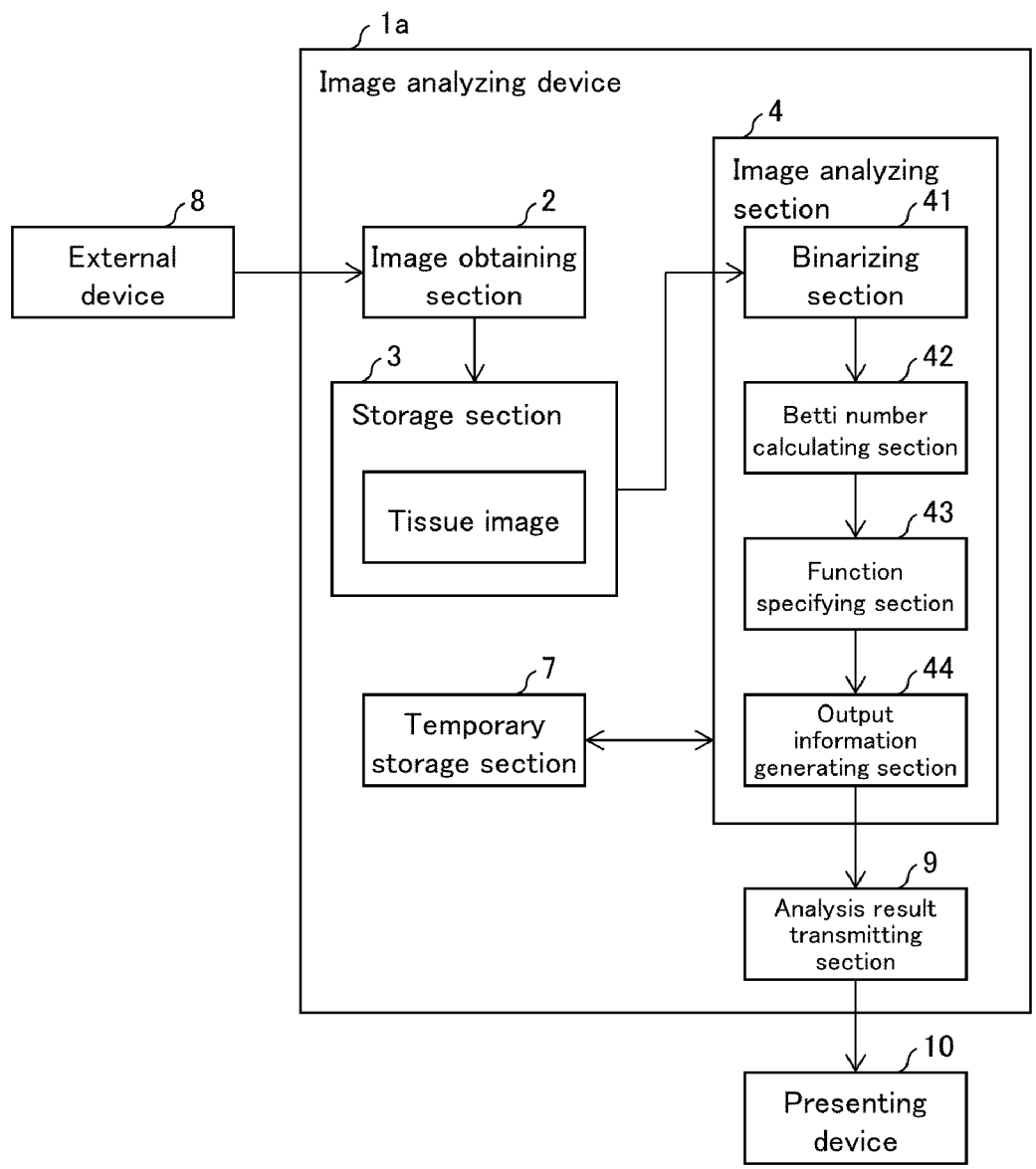

FIG. 12 is a block diagram illustrating an example configuration of an image analyzing device in accordance with Embodiment 2 of the present invention.

Figure 13:
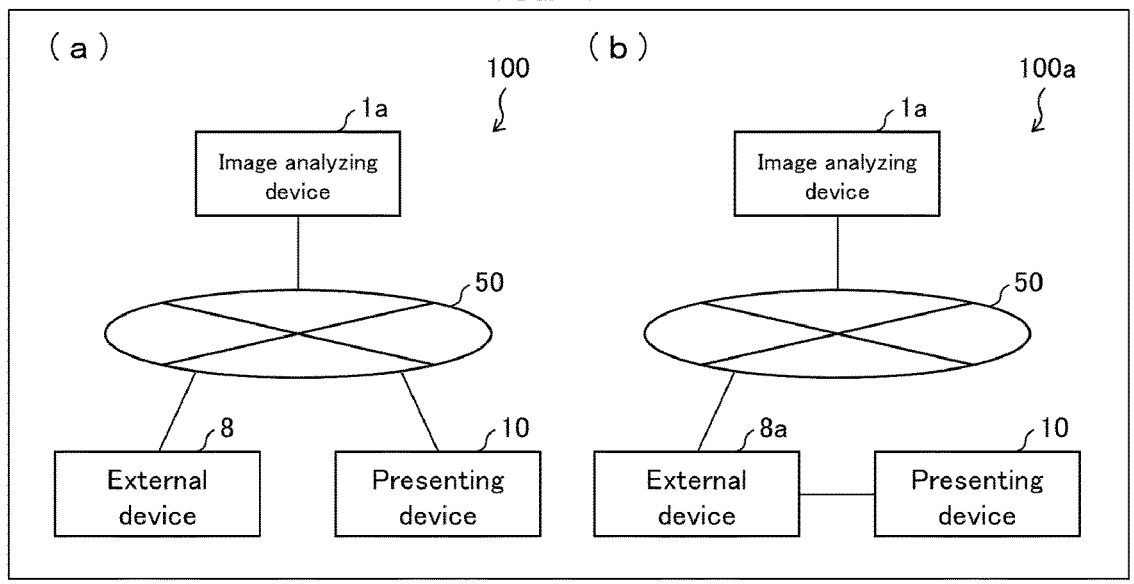

FIG. 13 is a view schematically illustrating example configurations of image analyzing systems each including an image analyzing device in accordance with Embodiment 2 of the present invention.

Figure 14:
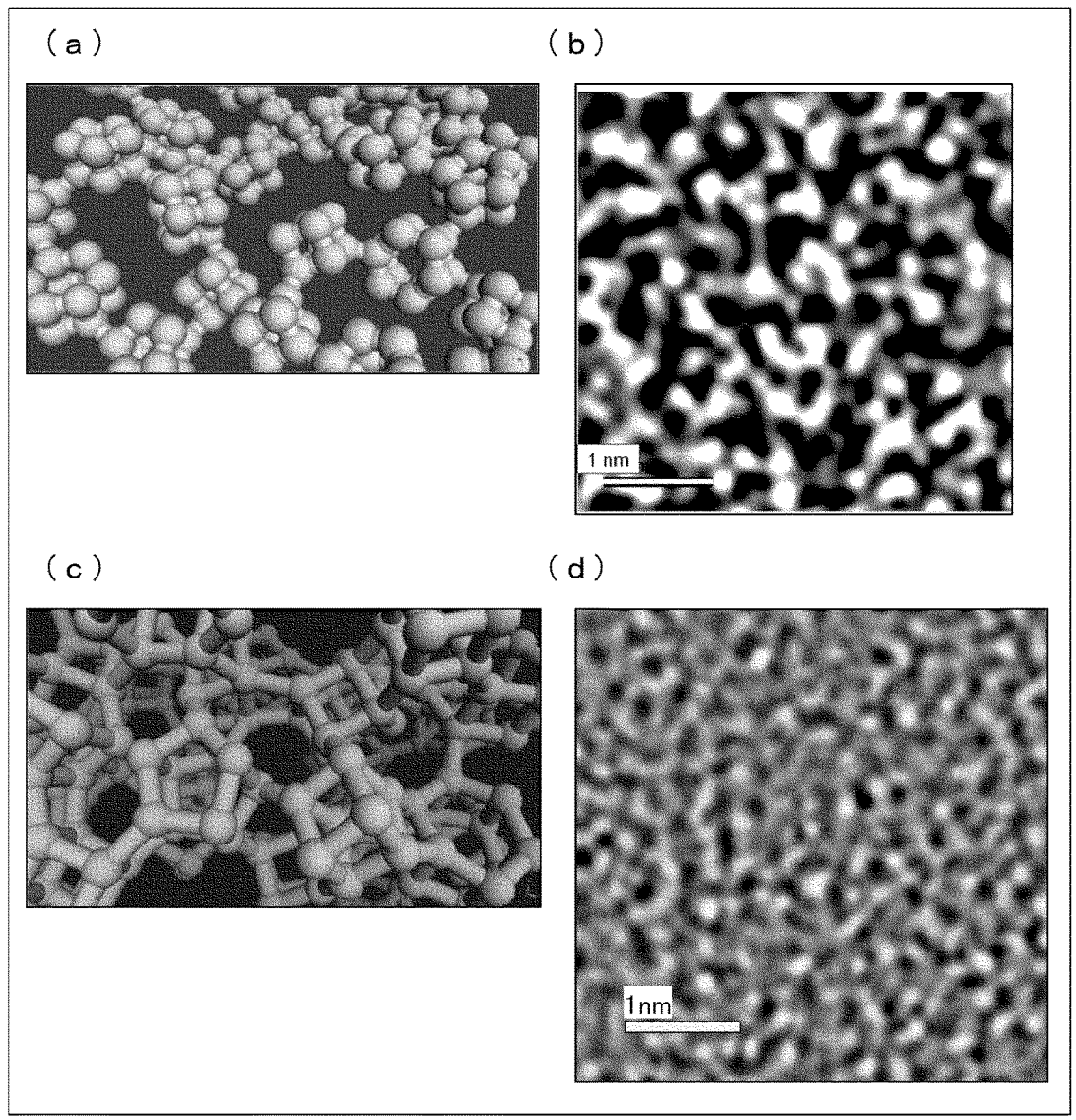

(a) of FIG. 14 is a view illustrating a molecular structure of a silicone gel which is obtained by carrying out gelation under an acidic condition. (b) of FIG. 14 is an image which is obtained by capturing, with use of a transmission electron microscope, the silicone gel that is obtained by carrying out the gelation under the acidic condition. (c) of FIG. 14 is a view illustrating a molecular structure of a silicone gel which is obtained by carrying out gelation under an basic condition. (d) of FIG. 14 is an image which is obtained by capturing, with use of a transmission electron microscope, the silicone gel that is obtained by carrying out the gelation under the basic condition.

Figure 15:
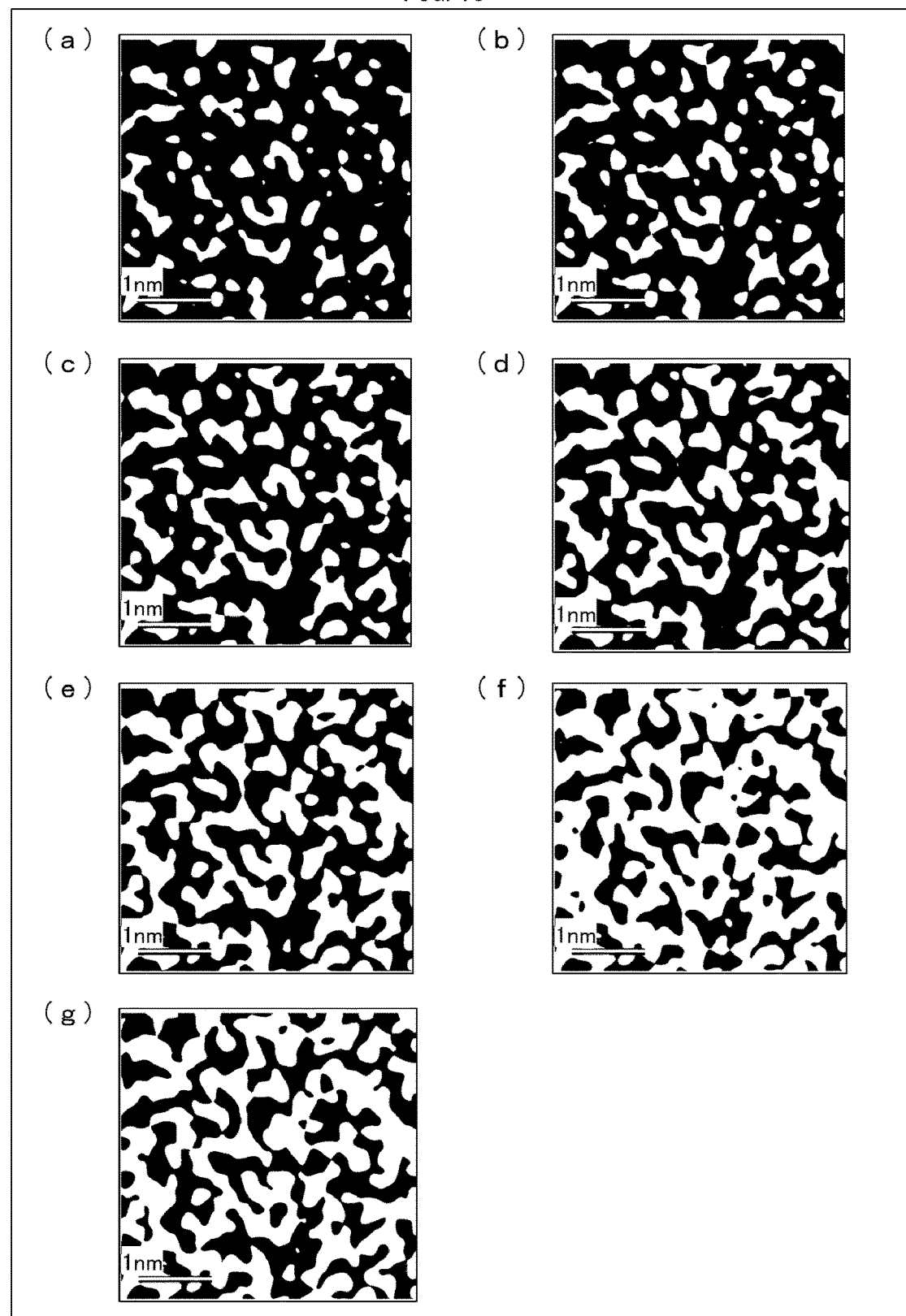

(a) through (g) of FIG. 15 are binarized images which are generated by binarizing the image of (b) of FIG. 14 while making binarization reference values differ from each other.

Figure 16:
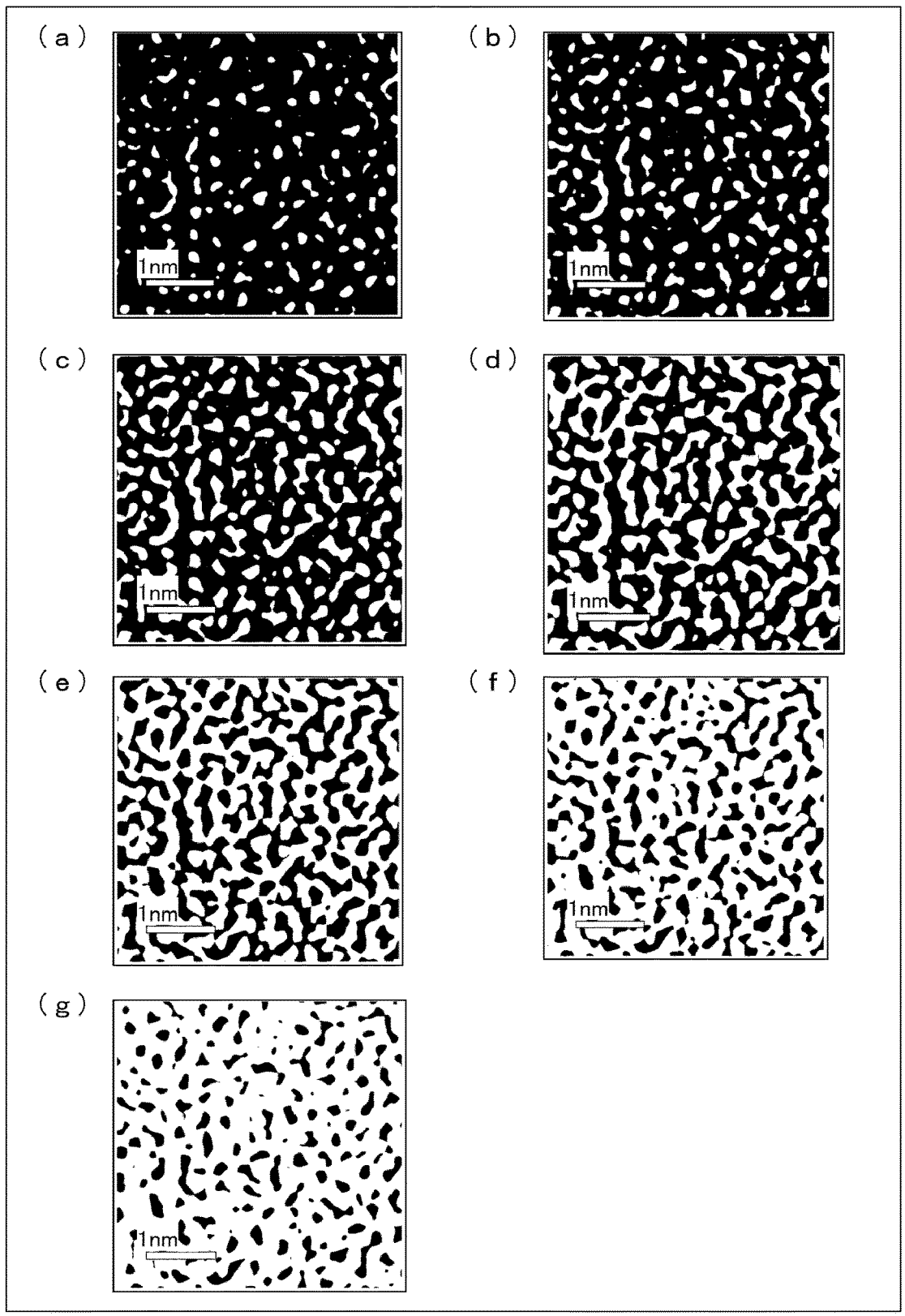

(a) through (g) of FIG. 16 are binarized images which are generated by binarizing the image of (d) of FIG. 14 while making binarization reference values differ from each other.

Figure 17:
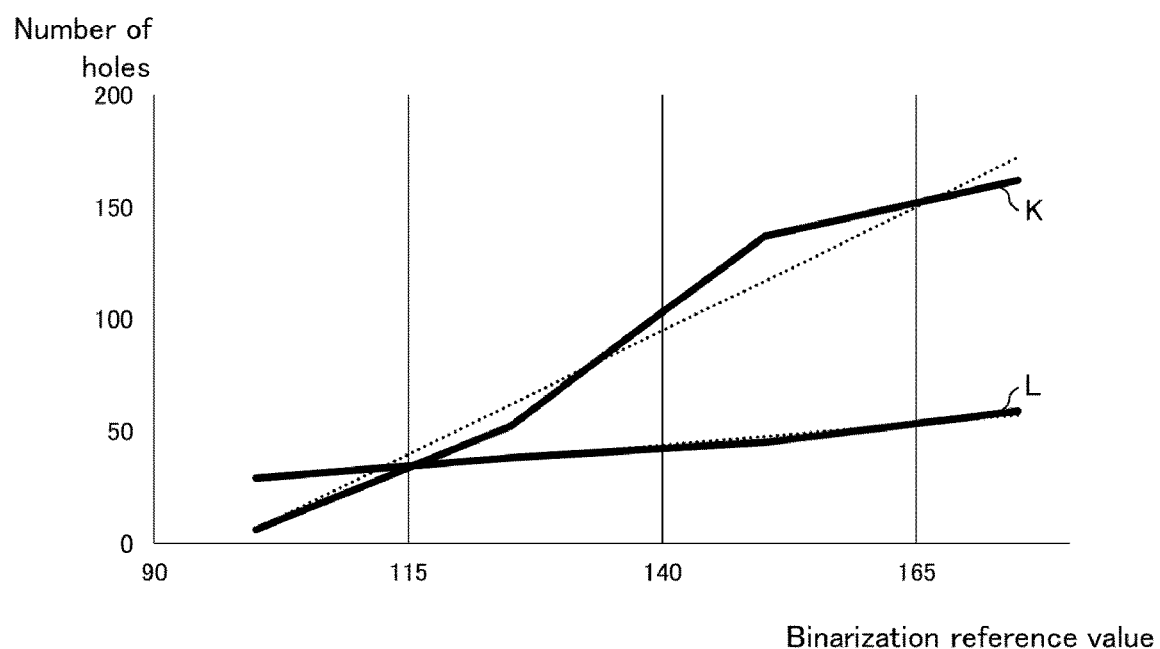

FIG. 17 is a view illustrating an example of a result of analyzing composition of the silicone gel.

DESCRIPTION OF EMBODIMENTS

The following description will discuss an embodiment of the present invention with reference to FIGS. 1 through 10.

(Technical Idea Concerning Present Invention)

First, a technical idea on the present invention will be described below. An object of the present invention is to (i) analyze a captured image which is obtained by capturing a tissue and (ii) output information useful in discriminating a degree of differentiation of a cancer captured in the captured image.

The inventors of the present invention checked a captured image of a tissue sample, and compared and studied, in detail, sizes and shapes of respective cancer cells or a positional relationship between respective cells. The inventors carried out binarization with respect to a tissue image of a tissue having a cancer, while making the respective reference binarization values differ from each other. The inventors then found it possible to discriminate a degree of differentiation of the cancer based on a relationship between (i) the respective binarization reference values and (ii) respective one-dimensional Betti numbers each of which was indicated by a corresponding image of the tissue which is included in a corresponding binarized image obtained by binarizing the tissue image with use of a corresponding binarization reference value.

Note that an image analyzing device 1 in accordance with each embodiment of the present invention is applicable to an analysis of composition of each of various kinds of structures such as a tissue of a living body, a mineral structure, and a structure of which a resin product is made. Note that a "structure" means a unit in which a plurality of kinds of constituents aggregate in a given pattern. A structure to be analyzed in each embodiment of the present invention can be a tissue of a living body which tissue is made of an aggregate of cells and the like, a mineral structure which is made of an aggregate of crystal grains, a structure of which a resin product is made and which is made of an aggregate of resin materials such as a silicone, or the like.

An example will be described below in which the image analyzing device 1 outputs information useful for discrimination of a degree of differentiation of a cancer which occurs in a tissue of a living body. Note, however, that a structure to be analyzed in each embodiment of the present invention is not limited to such a tissue.

<Degree of Differentiation of Cancer>

As a cancer cell occurring in a tissue unusually grows, cells become deformed and intrinsic composition of the tissue is lost. This causes the tissue to be changed into a state where cancer cells are disorderly scattered. According to a pathological diagnosis, a "degree of differentiation" of a cancer is specified based on such a morphological finding with regard to a tissue and/or cells.

A tissue of a living body includes, as constituents, cells each having a specific morphology and a specific function. The constituents work in cooperation with each other, so that the tissue fulfills its intrinsic function. The constituents, which are located in a normal region of the tissue, therefore have strong ties with each other, so that the tissue fulfills its intrinsic function.

In contrast, the constituents, which are located in a region of the tissue in which region a tumor or a cancer occurs, have a poor relationship therebetween, as compared with those located in the normal region, due to an increase in impurities and/or an abnormal increase in cells. If canceration of the tissue further progresses, then the tissue goes into a state where the constituents are dedifferentiated (poorly differentiated, moderately differentiated), that is, composition of the tissue is lost.

<Mathematical Representation for Quantification of Relationship between Constituents>

The inventors of the present invention attempted to apply, to quantification of a relationship between constituents of a tissue, a concept of homology, in particular, persistent homology. Homology is one of mathematical fields which facilitates an analysis of, for example, connection between figures by substituting an algebraic expression for morphological characteristics of the figures. In particular, the inventors of the present invention focused their attention on use of a one-dimensional Betti number among homology concepts.

The homology concept, which is a mathematical concept indicative of contact between constituents, allows for assessing a degree of contact between constituents of a tissue, in a case of (i) setting, in a pathological image, an appropriate binarization reference value (hereinafter, also referred to as a binarization parameter) and (ii) calculating, from a binarized image, a one-dimensional Betti number per unit area of the binarized image.

A Betti number is a topological pointer number which is independent of a shape of each of figures (constituents) but is dependent on merely contact and separation between figures. In a case where a q-th singular homology group is finitely generated, the q-th singular homology group can be expressed by a direct sum of a free Abelian group and a finite Abelian group. A rank of the free Abelian group is called a "Betti number." In a case of two dimensions, a zero-dimensional Betti number indicates the number of connected components. A one-dimensional Betti number indicates the number of spaces (hole-shaped regions) surrounded by a connected component(s). In other words, the one-dimensional Betti number indicates the number of "holes" formed by the connected component(s).

<One-Dimensional Betti Number>

A one-dimensional Betti number is mathematically defined as follows. Here, a figure (one-dimensional complex) K obtained by connecting a finite number of line segments is assumed. In general, a one-dimensional Betti number of the figure K is "r," in a case where (i) the number of connected components of the figure K remains unchanged even in a case where any r one-dimensional simplices (line segments), each of which does not have both ends, are removed from the figure K and (ii) the number of connected components of the figure K is increased by one (1) in a case where any (r+1) one-dimensional simplices (line segments), each of which does not have both ends, are removed from the figure K.

Figure 2:
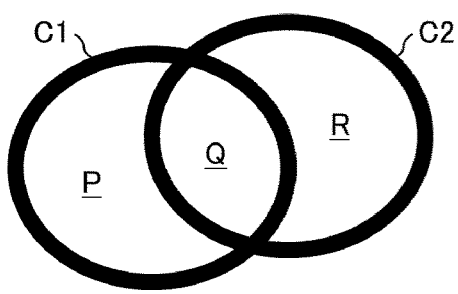
FIG. 2 is a view illustrating a one-dimensional Betti number applicable to the image analyzing device in accordance with Embodiment 1 of the present invention.

The one-dimensional Betti number will be described below with reference to a figure illustrated in FIG. 2. FIG. 2 is a view illustrating a Betti number applicable to the image analyzing device 1 in accordance with an embodiment of the present invention. According to FIG. 2, a circle C1 and a circle C2 intersect with each other. The number of "holes" which this figure has is three. A one-dimensional Betti number is calculated as 3. Calculation of a one-dimensional Betti number of a figure is thus equivalent to counting of the number of "holes" which the figure has.

Embodiment 1

(Configuration of Image Analyzing Device 1)

Figure 1:
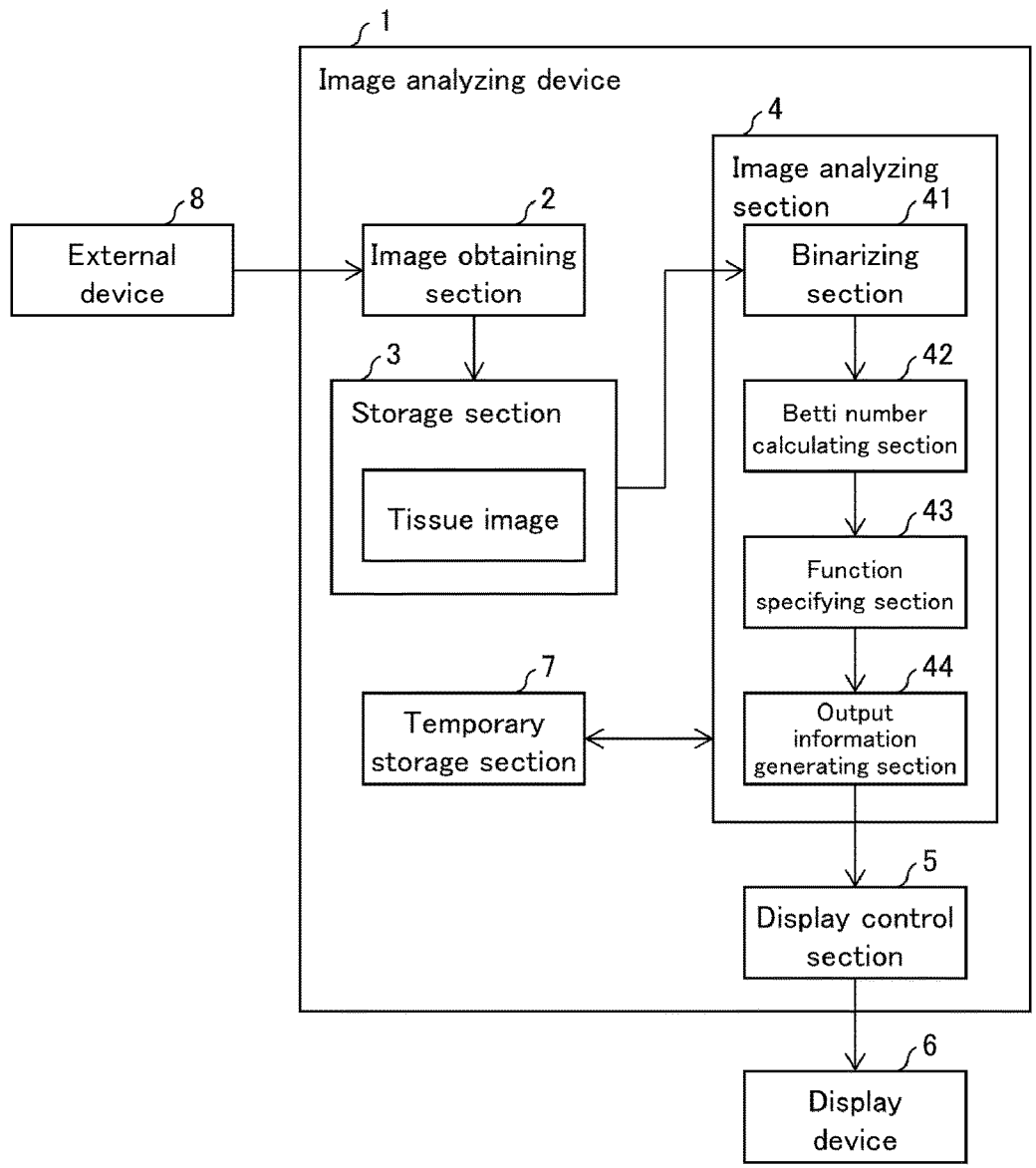
FIG. 1 is a block diagram illustrating an example configuration of an image analyzing device in accordance with Embodiment 1 of the present invention.

A configuration of an image analyzing device 1 will be described below with reference to FIG. 1. FIG. 1 is a block diagram illustrating an example configuration of an image analyzing device 1 in accordance with Embodiment 1 of the present invention. As illustrated in FIG. 1, the image analyzing device 1 includes an image obtaining section 2 (receiving section), a storage section 3, an image analyzing section 4 (image analyzing device), a display control section 5, and a temporary storage section 7. Note that, although FIG. 1 illustrates an example in which the image analyzing device 1 is connected to a display device 6 (presenting section) that is provided separately from the image analyzing device 1, the image analyzing device 1 is not limited to such a configuration. For example, the image analyzing device 1 can be configured so as to include therein the display device 6 (presenting section). Alternatively, the image analyzing device 1 can be configured so as to be connected to a plurality of display devices 6 by wire or wireless.

The image obtaining section 2 obtains, from an external device 8 (such as an image capturing device, which is connected to a microscope, or a storage device, in which image data can be stored), a captured image which is obtained by capturing a tissue (hereinafter, referred to as a tissue image), and then stores the tissue image thus obtained in the storage section 3. The tissue image is an image obtained by capturing the tissue at an appropriate magnification. Note that a magnification at which a tissue to be analyzed is captured can be set as appropriate by a person skilled in the art, depending on the tissue. Note also that the tissue image can be an image obtained by capturing the tissue as it is or can be alternatively an image obtained by capturing the tissue which has been stained appropriately.

How to stain a tissue is not limited in particular. In a case of a tissue of a living body, HE (Hematoxylin-Eosin) staining can be, for example, employed. In a case where a tissue is subjected to the HE staining, cell nuclei and cytoplasm are stained. Therefore, the HE staining is suitable for observing a relationship between cells of a tissue.

The storage section 3 stores therein (1) a tissue image which the image obtaining section 2 has obtained, (2) a control program for controlling each section, which control program is executed by the image analyzing section 4, (3) an OS program, (4) an application program, and (5) various sets of data which are read out in a case where the image analyzing section 4 executes the programs. The storage section 3 is constituted by a nonvolatile storage device such as a hard disk or a flash memory.

The temporary storage section 7 is used as a working area in which data is temporarily stored while the programs are being executed. The temporary storage section 7 is constituted by a volatile storage device such as an RAM (Random Access Memory).

The display control section 5 controls the display device 6 to display, for example, an image (output information) indicative of a result of an analysis which result has been outputted by the image analyzing section 4.

The display device 6 is a display device which displays output information and the like that have/has been outputted by the image analyzing section 4. Examples of the display device 6 encompass a liquid crystal display device. Note that the image analyzing device 1 can be configured so as to include a dedicated display device 6. Note also that the display device 6 can have a configuration in which a touch sensor is provided on a display screen of the display device 6 so that the display device 6 detects a touch operation conducted, by a user, on a surface of the display screen.

(Configuration of Image Analyzing Section 4)

The image analyzing section 4 analyzes a tissue image obtained by the image obtaining section 2, and then outputs information indicative of a degree of differentiation of a cancer tissue captured in the tissue image. The image analyzing section 4 includes a binarizing section 41 (dividing section), a Betti number calculating section 42 (space number calculating section), a function specifying section 43 (specifying section), and an output information generating section 44.

The binarizing section 41 binarizes a tissue image such that (i) white color is displayed by a pixel having a pixel value greater than a binarization reference value and (ii) black color is displayed by a pixel having a pixel value equal to or smaller than the binarization reference value. The binarizing section 41 generates a plurality of binarized images by binarizing, a plurality of times, a single tissue image, which is obtained by capturing a tissue, while making binarization reference values differ from each other.

An example method of determining the binarization reference values will be described below. Based on distribution data (histogram) on pixel values corresponding to a given color component of a tissue image, the binarizing section 41 specifies, as a standard pixel value, a pixel value which corresponds to the given color component and which is the most in number or the highest in frequency of appearance, out of the pixel values. The binarizing section 41 then determines, as the binarization reference values, values obtained by multiplying the standard pixel value by scales each falling within a given range (for example, 0.55 to 0.72).

The binarizing section 41 carries out binarization, by use of a plurality of binarization reference values thus determined, with respect to a grayscale image of a tissue image so as to generate a plurality of binarized images.

Note that the binarization reference values, which are used to carry out the binarization with respect to a tissue image, are important in detecting outer edges of constituents captured in the tissue image so as to determine a relationship between the constituents. White color is displayed by a pixel which has a pixel value greater than the binarization reference value. Black color is displayed by a pixel which has a pixel value equal to or smaller than the binarization reference value. It follows that, in a case where the tissue image is binarized with use of an excessively great binarization reference value, borderlines are excessively emphasized. This causes a blackish binarized image to be displayed. In a case where the tissue image is binarized with use of an excessively small binarization reference value, a whitish binarized image having few borderlines is displayed (see FIG. 5). The binarization which is carried out with respect to a tissue image will be later described in detail.

The binarizing section 41 can further serve as an image dividing section (dividing section) that divides a tissue image, which is obtained by the image obtaining section 2, into divided regions each having a given size (hereinafter, may be also referred to as "divided images"). Alternatively, the image analyzing section 4 can be configured so as to further include an image dividing section (not illustrated), in addition to the binarizing section 41, the Betti number calculating section 42, the function specifying section 43, and the output information generating section 44. The binarizing section 41 can carry out binarization in which ranges, within which the binarization reference values are made differ from each other, are determined with respect to the respective divided regions. Note, however, that in a case where a target region of the tissue image is discriminated while the divided regions are being compared with each other, it is desirable to carry out the binarization with respect to all of the divided regions, while the ranges, within which the binarization reference values are made differ from each other, are identical to each other.

The Betti number calculating section 42 calculates, with respect to each of a plurality of binarized images which are generated by the binarizing section 41, the number of holes each of which is surrounded by a closed outer edge of a constituent or by respective portions of closed outer edges of a plurality of constituents (i.e., the number of hole-shaped regions). That is, the Betti number calculating section 42 calculates a one-dimensional Betti number of a figure of a tissue which figure is included in each binarized image.

Each of the holes is an opening which has, as its outer edge, at least part of an outer edge of at least one constituent (in a case of a single constituent, an entire outer edge of such a single constituent). In other words, the holes are classified into (1) a hole which a single constituent has therein and (2) a hole which is surrounded by respective portions of outer edges of a plurality of constituents connected to each other.

An existing program can be employed as the Betti number calculating section 42. Examples of the exiting program encompass CHomP. The CHomP is freeware in compliance with a GNU (General Public License), and is available from a web site (http://chomp.rutgers.edu/). Note, however, that any program other than the CHomP can be employed, provided that a one-dimensional Betti number can be calculated from an image.

The function specifying section 43 specifies a numerical value (characteristic numerical value) which characterizes a correspondence between (i) respective binarization reference values and (ii) the respective numbers of holes. The function specifying section 43 only needs to specify at least one numerical value. For example, the function specifying section 43 can (i) derive an expression which represents a function (approximate function) that approximately indicates a relation between (a) respective binarization reference values and (b) the respective numbers of holes and (ii) specify, as a characteristic numerical value, at least one of coefficients included in the expression thus derived. In such a case, the function specifying section 43 calculates (specifies) one or more numerical values (characteristic numerical values) which represent a characteristic of the function that approximately indicates a change in number of holes in response to a change in binarization reference value. Note, here, that the above function (approximate function) can be a function which can be represented by any relational expression. For example, the function can be an n-th degree function (n is equal to or greater than 1) (including linear approximation and log approximation), an exponential function (power approximation), or a trigonometric function. The following description will take, as an example, a case where the function specifying section 43 calculates a plurality of coefficients, including an n-th degree coefficient (characteristic numerical value), which are included in an expression (n-th degree expression) that represents an n-th degree function (n is equal to or greater than 1) approximately indicating a change in number of holes in response to a change in binarization reference value.

Note that the function specifying section 43 can be configured so as to, instead of deriving an approximate function, specify a plurality of characteristic numerical values which characterize a correspondence between (i) respective binarization reference values and (ii) the respective numbers of holes. For example, the function specifying section 43 can employ a technique such as deep learning so as to specify a characteristic numerical value which characterizes a correspondence between (i) respective binarization reference values and (ii) the respective numbers of holes. For example, the function specifying section 43 can employ deep learning which employs, as learning data, a plurality of combinations each of which is a combination of (a) a typical image (such as a tissue image) having a given characteristic (such as a degree of differentiation of a cancer) and (b) a characteristic numerical value corresponding to a correspondence between (i) respective binarization reference values used for the typical image to be binarized and (ii) the respective numbers of holes, the numbers being obtained from respective binarized images obtained by binarizing the typical image. Note, here, that the characteristic numerical value, which can be employed as the learning data, is not limited to a specific one, provided that the characteristic numerical value corresponds to a correspondence between (i) respective binarization reference values and (ii) the respective numbers of holes. For example, the characteristic numerical value can be any numerical value, indicative of a degree of differentiation of a cancer (tissue), such as 1 (one) in a case of a well differentiated cancer, 2 (two) in a case of a moderately differentiated cancer, or 3 (three) in a case of a poorly differentiated cancer. In a case where such deep learning is employed, the function specifying section 43 is capable of specifying an appropriate characteristic numerical value, instead of deriving an expression which represents a function that approximately indicates a correspondence between (i) respective binarization reference values and (ii) the respective numbers of holes.

The output information generating section 44 generates output information corresponding to at least one of a plurality of characteristic numerical values (for example, coefficients of an approximate function) which the function specifying section 43 has calculated. Examples of the output information encompass information (output information) which reflects a position of a point (hereinafter, referred to as a coordinate point), having, as coordinates, a plurality of coefficients calculated by the function specifying section 43, in a coordinate space formed by a plurality of coordinate axes which correspond to the respective plurality of coefficients calculated by the function specifying section 43. Furthermore, the output information generating section 44 can be configured so as to generate, as the output information, an image for determination (hereinafter, referred to as a determination-purpose image) in which determination-purpose image divided regions are shown. In such a configuration, the output information generating section 44 can change how to show the divided regions in the determination-purpose image, depending on positions of coordinate points corresponding to the respective divided regions of a captured image (see (b) of FIG. 11). The output information generating section 44 can display the divided regions so that one divided region differs from the other. For example, (a) a divided region, including a poorly differentiated cancer, is displayed in red, (b) a divided region, including an adenoma, is displayed in orange, and (c) a divided region, including a well differentiated cancer, is displayed in yellow so that (i) the divided regions each including such a cancer or tumor and (ii) a divided region including neither cancer nor tumor are clearly differentiated from each other.

Note that the output information generating section 44 can generate, as output information, (1) a combination of a plurality of numerical values indicative of the coordinate point, (2) a graph in which the coordinate point is shown (for example, a distribution diagram illustrated in (b) of FIG. 10), (3) information (such as a character, a numerical value, and color information) indicative of a degree of differentiation of a cancer which degree is discriminated based on the position of the coordinate point. In a case where there are a plurality of divided regions, information, which specifies a divided region which has been analyzed, is preferably included in each of those pieces of output information.

(Flow of Process Carried Out by Image Analyzing Device 1)

Next, an example flow of a process, carried out by the image analyzing device 1, will be described below with reference to FIG. 3. FIG. 3 is a flowchart illustrating an example process flow carried out by an image analyzing device 1. Note that the following description will be given on the premise that a tissue image is already stored in a storage section 3. Note also that an example will be described below in which the process includes generating divided regions by dividing the tissue image.

First, a binarizing section 41 obtains the tissue image from the storage section 3, and then divides the tissue image thus obtained into divided regions each having a given size (S1). Note that the divided regions are obtained by dividing the tissue image in a 3-by-3 matrix, a 5-by-5 matrix, or the like.

The binarizing section 41 then generates a plurality of binarized images from such a single tissue image by binarizing the single tissue image while making binarization reference values differ from each other (S2: binarizing step). Note that how the binarizing section 41 generates binarized images from a tissue image will be later described.

Various kinds of figures are represented in a bit-mapped format by employing many picture elements, called pixels, whose light intensities vary depending on image data, the pixels each having a square shape. According to binarization of a tissue image, (i) in a case where a light intensity is greater than a given intensity, a pixel displays black color, which is recognized as 1 (one) by a computer and (ii) in a case where the light intensity is equal to or lower than the given intensity, the pixel displays white color, which is recognized as 0 (zero) by the computer.

The binarizing section 41 supplies the plurality of binarized images to a Betti number calculating section 42.

The Betti number calculating section 42 calculates a one-dimensional Betti number for each of the divided regions shown in each of the plurality of binarized images thus received (S3: space number calculating step). The Betti number calculating section 42 supplies one-dimensional Betti numbers thus calculated to a function specifying section 43.

The function specifying section 43 calculates a plurality of coefficients included in a relational expression which indicates a correspondence between (i) the respective binarization reference values and (ii) the respective one-dimensional Betti numbers supplied from the Betti number calculating section 42 (S4: function specifying step). The function specifying section 43 supplies, to an output information generating section 44, the plurality of coefficients such that the plurality of coefficients are associated with information which specifies a corresponding one of the divided regions.

For each of the divided regions, the output information generating section 44 specifies, in a coordinate space, a position of a coordinate point which has, as coordinates, the plurality of coefficients calculated by the function specifying section 43. The output information generating section 44 then generates output information (for example, the above-described determination-purpose image) corresponding to the position thus specified (S5: output information generating step). The output information generating section 44 supplies the output information thus generated to a display control section 5.

The display control section 5 controls a display device 6 to display the output information supplied from the output information generating section 44 (S6).

(Flow of Process of Generating Binarized Images)

Next, the following description will discuss, with reference to FIG. 4, how the binarizing section 41 generates binarized images from a tissue image. FIG. 4 is a flowchart illustrating an example process flow in which binarized images are generated by an image analyzing device 1 in accordance with Embodiment 1 of the present invention.

The binarizing section 41 obtains pixel values corresponding to each of color components (for example, RGB) which pixel values are included in image data of a tissue image, and then determines a standard pixel value based on which binarization reference values are set (S11). For example, in a case where the tissue image is an image obtained in a case where a tissue section, which has been subjected to the HE staining, is captured, the standard pixel value is determined based on pixel values corresponding to blue (B) out of the color components RGB. A specific example of a method of determining a standard pixel value will be described below.

In a case where a tissue is subjected to the HE staining, cell nuclei are stained blue. In a case where a tissue image is analyzed while the cell nuclei are being focused on, it is suitable to determine binarization reference values on the basis of pixel values corresponding to B. In a case where a tissue is stained, the tissue may not be stained evenly. It is therefore preferable to determine the binarization reference values with reference to a region of the tissue which region is normally stained. Accordingly, out of the pixel values corresponding to B constituting the tissue image, a pixel value which is the highest in frequency of appearance is determined as a standard pixel value. In a case where a plurality of captured images, which are obtained by capturing respective tissues that are stained to respective different degrees, are used, it is possible to standardize the degrees by determining the binarization reference values as described above.

Specifically, in distribution data which indicates a relationship between (i) respective pixel values corresponding to B and (ii) the respective numbers (pixel number) of pixels having such pixel values, a standard pixel value is specified. The standard pixel value corresponds to a pixel value at which the pixel number becomes a local maximum. That is, the standard pixel value corresponds to a pixel value which is the highest in frequency of appearance, out of the pixel values corresponding to B constituting the tissue image. Note that, in a case where there are a plurality of pixel values at which pixel numbers become respective local maximums, it is only necessary that the greatest pixel value be selected.

The following description will discuss a case where the binarization reference values are determined based on the pixel values corresponding to B. Note, however, that the binarization reference values can be alternatively determined based on pixel values corresponding to red (R) or green (G) out of the color components RGB, depending on (i) distribution of the color components of the tissue image or (ii) a color tone of a pigment used in staining.

Next, the binarizing section 41 generates a plurality of binarized images from a grayscale image of the tissue image (S12). In so doing, binarization reference values are employed which are obtained by multiplying the standard pixel value, determined in S11, by various scales which fall within a given range. This allows a plurality of binarized images to be generated from a single tissue image, while making binarization reference values differ from each other. Note that it is possible to change the scales as appropriate depending on composition of a tissue to be analyzed, the scales being used to find the binarization reference values which are employed when a plurality of binarized images are generated from a single tissue image.

Note, however, that, in a case where a tissue image is binarized with use of an excessively great binarization reference value, borderlines are excessively emphasized. This causes a blackish binarized image to be displayed. In contrast, in a case where the tissue image is binarized with use of an excessively small binarization reference value, a whitish binarized image having few borderlines is displayed. This will be described below with reference to FIG. 5.

(a) of FIG. 5 is an original tissue image. According to the original tissue image, a pixel value (standard pixel value) which is the highest in frequency of appearance (which becomes a local maximum) in distribution data on pixel values corresponding to B is 171 (one hundred seventy one). (b) of FIG. 5 is a view illustrating an example binarized image which is obtained by binarizing the original tissue image with use of, as a binarization reference value, a value obtained by multiplying, by 1 (one), the standard pixel value corresponding to B. (c) of FIG. 5 is a view illustrating an example binarized image which is obtained by binarizing the original tissue image with use of, as a binarization reference value, a value obtained by multiplying, by 0.7 (zero point seven), the standard pixel value corresponding B. (d) of FIG. 5 is a view illustrating an example binarized image which is obtained by binarizing the original tissue image with use of, as a binarization reference value, a value obtained by multiplying, by 0.5 (zero point five), the standard pixel value corresponding to B. In a case where the standard pixel value, corresponding to B, is employed as it is (that is, a scale is equal to 1 (one)) as a binarization reference value so that the original tissue image is binarized, a binarized image is blackish, and is therefore not suitable for assessment of a relationship between constituents (see (a) of FIG. 5).

In a case where the scale is 0.5, a binarized image is whitish and is also not suitable for the assessment of the relationship between the constituents (see (c) of FIG. 5). (b) of FIG. 5 is an image obtained in a case where the scale is 0.7. The image illustrated in (b) of FIG. 5 is suitable for the assessment of the relationship between the constituents of a tissue. According to an excessively blackish or excessively whitish binarized image, an excessively small one-dimensional Betti number is calculated. Accordingly, a value indicative of the relationship between the constituents is not appropriately calculated.

The inventors thus studied, with regard to various scales, whether or not binarized images were suitable, and found the following. That is, in order to discriminate, based on an analysis of an image of a tissue of a living body which tissue has been subjected to the HE staining, a degree of differentiation of a cancer in the tissue of the living body, the scale, by which the standard pixel value corresponding to B is multiplied, is preferably selected from a range of not lower than 0.55 and not higher than 0.72.

By thus limiting, to a preferable range, a range within which the binarization reference values fall, it is possible to increase a processing speed of the image analyzing device 1.

Note that it is possible to alter as appropriate how to determine the binarization reference values, depending on a kind of a tissue, a method of staining the tissue, and/or the like. A color component, based on which the standard pixel value is specified, can be a color component other than B (blue). Furthermore, the scale, by which the standard pixel value is multiplied, can be a value which falls within any appropriate range.

Note that a method of determining the binarization reference values, with use of which the binarizing section binarizes a tissue image, as thresholds common to (fixed for) all of the pixels can be employed or a method of determining the binarization reference values as thresholds variable for each of the pixels can be alternatively employed. The following methods (1) through (4) are, for example, each known as the method of determining the binarization reference values as thresholds common to (fixed for) all of the pixels:

(1) a method in which (i) an image to be binarized is converted into a grayscale image with use of luminance information on the image and then (ii) binarization reference values are determined based on a pixel value (peak value) which is the highest in frequency of appearance (which becomes a local maximum) in distribution data on pixel values of the grayscale image;

(2) a method in which (i) an RGB image is subjected to H(hue)S(saturation)V(value) conversion or H(hue)L(lightness)S(saturation) conversion and (ii) binarization reference values are determined based on a histogram of V (value), S (saturation), or the like;

(3) a method in which binarization reference values are determined by analyzing bimodality of distribution data on pixel values and obtaining a solution which maximizes a degree of separation, instead of determining, as a threshold, a pixel value itself which is the highest in frequency of appearance (which becomes a local maximum) in the distribution data (for example, Otsu thresholding); and (4) a method in which (i) a proportion of an image to be binarized to a whole image (i.e., a proportion of the number of pixels corresponding to the image to be binarized to the whole pixels corresponding to the whole image) is specified by a percentage or the like and then (ii) binarization reference values are determined (example: percentile method).

(Example Analysis of Tissue Image)

The following description will discuss, with reference to FIGS. 6 through 8, an example in which a tissue image, which had been obtained by capturing a tissue of a living body, was analyzed with use of an image analyzing device 1 in accordance with Embodiment of the present invention. FIGS. 6 through 8 are views each illustrating an example of a result of an analysis carried out with use of an image analyzing device 1. FIG. 6 illustrates an example of a result of an analysis of a normal tissue. FIGS. 7 and 8 each illustrate an example of a result of an analysis of a tissue including a cancer.

In order that a plurality of binarized images were generated by binarizing a tissue image illustrated in (a) of FIG. 6, binarization reference values were obtained by multiplying a standard pixel value, corresponding to B, by values which were differed from 0.55 to 0.72 in increments of 0.01. A plurality of binarized images were then generated from a grayscale image of the tissue image with use of the respective binarization reference values thus obtained, and one-dimensional Betti numbers were calculated for each of the plurality of binarized images.

A divided region A and a divided region B of the tissue image illustrated in (a) of FIG. 6 were each a normal region which did not include any cancer. (b) of FIG. 6 illustrates a graph obtained by plotting a variation in one-dimensional Betti number in each of the divided regions A and B, which variation was caused by a variation in binarization reference value. Note that, in each of (b) of FIG. 6, (b) of FIG. 7, and (b) of FIG. 8, a horizontal axis indicates scales by which the standard pixel value corresponding to B was multiplied, and a vertical axis indicates the numbers of holes (that is, one-dimensional Betti numbers). As is clear from (b) of FIG. 6, in each of the divided regions A and B, it was possible to approximate the numbers of holes with respect to the respective scales, with use of a quadratic function (dotted line illustrated in (b) of FIG. 6) which is an approximate expression (expression which represents an approximate function). Each correlation coefficient ($R^2$), indicative of a degree of approximation, was higher than 0.99. This ensures that the approximation was considerably accurate.

Note that the example, in which the quadratic function was used as the approximate expression, has been described here but the approximate expression is not limited to the quadratic function. For example, the quadratic function can be substituted with any high-degree function such as a cubic function or a quartic function. The quadratic function can be substituted with a linear function, depending on a tissue. Any software, such as an algorithm incorporated in Microsoft Excel (registered trademark), can be employed to plot a regression curve and derive an approximate expression.

Next, an example in which a region including a cancer was analyzed will be described. A divided region C and a divided region D of a tissue image (see (a) of FIG. 7) were each a region including a cancer. (b) of FIG. 7 illustrates a graph obtained by plotting a change in one-dimensional Betti number in each of the divided regions C and D, which change was caused in response to a change in binarization reference value. As is clear from (b) of FIG. 7, in each of the divided regions C and D, it was also possible to approximate, with considerably high accuracy, the numbers of holes with respect to respective scales, with use of a quadratic function (dotted line illustrated in (b) of FIG. 7).

Divided regions E through G of a tissue image (see (a) of FIG. 8) were each a region including a cancer. (b) of FIG. 8 illustrates a graph obtained by plotting a change in one-dimensional Betti number in each of the divided regions E through G, which change was caused in response to a change in binarization reference value. As is clear from (b) of FIG. 8, in each of the divided regions E through G, it was also possible to approximate, with considerably high accuracy, the numbers of holes with respect to respective scales, with use of a quadratic function (dotted line illustrated in (b) of FIG. 8).

(Case where Quadratic Coefficient is Negative)

The following description will discuss, with reference to FIG. 9, a case where a quadratic coefficient of a quadratic function is negative. Many tissue images resulted in that quadratic coefficients of quadratic functions were positive. However, some tissue images resulted in that quadratic coefficients of quadratic functions were negative, as in the divided region E.

FIG. 9 is a graph illustrating ratios between (i) a case(s) where a quadratic coefficient of an approximate expression was positive and (ii) a case(s) where a quadratic coefficient of an approximate expression was negative. As illustrated in FIG. 9, some normal tissues, adenomas, and well differentiated cancers resulted in that quadratic coefficients were negative. On the other hand, moderately differentiated cancers and poorly differentiated cancers did not result in that quadratic coefficients were negative, except for one case. Besides, according to such a poorly differentiated cancer case in which the quadratic coefficient was negative, a state of a tissue image was poor and cell nuclei were crushed. That is, it became clear that (i) many adenomas and well differentiated cancers caused quadratic coefficients of approximate expressions to be negative and (ii) moderately differentiated and poorly differentiated cancers hardly caused quadratic coefficients of approximate expressions to be negative.

(Example of Application to Discrimination of Degree of Differentiation of Cancer)

The following description will discuss an example in which, with use of an image analyzing device 1, (i) a tissue image, which is obtained by capturing a tissue of a living body, is analyzed and (ii) information, in accordance with which a degree of differentiation of a cancer is discriminated, is extracted. FIG. 10 illustrates an example of a graph obtained by plotting a point (coordinate point) having, as coordinates, a plurality of coefficients of an approximate expression on an analyzed tissue image (or each divided image), in a coordinate space formed by a plurality of coordinate axes which correspond to the respective plurality of coefficients of the approximate expression. (a) of FIG. 10 illustrates a quadratic function employed as an approximate expression. (b) of FIG. 10 is a distribution chart obtained by plotting a coordinate point having, as coordinates, (i) a logarithm (Log "a") of a quadratic coefficient "a" of the approximate expression and (ii) "b" indicative of a position of an axis of the approximate expression. A base of the logarithm can be 10 or can be alternatively a natural number "e." Note that, since a value of the quadratic coefficient "a" of the approximate expression is great, the logarithm is used here for convenience, but the logarithm is not always necessary to be used.

As illustrated in (b) of FIG. 10, (i) a coordinate point obtained from an image including a moderately differentiated cancer and (ii) a coordinate point obtained from an image including a poorly differentiated cancer are distributed so as to be concentrated in a region where values of a vertical axis and values of a horizontal axis are both greater. Meanwhile, a coordinate point obtained from an image including a well differentiated cancer, a coordinate point obtained from an image including an adenoma, and a coordinate point obtained from an image including a normal tissue are distributed in respective regions having respective unique inclinations (see regions shown by respective ellipses in (b) of FIG. 10). (b) of FIG. 10 shows that the respective inclinations of the regions of the well differentiated cancer, the adenoma, and the normal tissue demonstrate a tendency to become gentler in this order.

Based on such a tendency of distribution of a coordinate point, it is possible to calculate an index indicative of a degree of differentiation of a cancer which is captured in a tissue image (or divided image) from which the coordinate point has been calculated. Based on the index thus calculated, it is possible to generate, as output information, a tissue image (determination-purpose image) in which a region, to which a doctor should direct his/her attention during his/her determining the cancer, is clearly specified. This output information is information useful in discriminating the degree of differentiation of the cancer.

(Determination-Purpose Image)

The following description will discuss a determination-purpose image with reference to FIG. 11. FIG. 11 is a view illustrating an example of a determination-purpose image. (a) of FIG. 11 illustrates a tissue image to be analyzed. (b) of FIG. 11 illustrates a determination-purpose image in which each of divided images is color-coded based on a degree of differentiation of a cancer captured in the tissue image.

For example, in (b) of FIG. 11, each of divided regions in regions H and I illustrated in (a) of FIG. 11 is color-coded based on a result of an analysis of the each of the divided regions (based on a position of a coordinate point). A divided region, which is likely to include a poorly differentiated cancer, can be displayed, for example, in red. A divided region, which is likely to include an adenoma, can be displayed, for example, in orange. A divided region, which is likely to include a well differentiated cancer, can be displayed, for example, in yellow. In a case where it is not possible to discriminate a single degree of differentiation (for example, in a case where a coordinate point is present in a region where doted regions overlap each other in (b) of FIG. 10), the degree of differentiation can be displayed by gradation.

(Discrimination of Moderately Differentiated Cancer and Well Differentiated Cancer from Each of which Negative Quadratic Coefficient is Obtained)

Note that, as has been described, there are some moderately differentiated and well differentiated cancers which result in approximate expressions including negative quadratic coefficients. In such a case, it is not possible to plot a coordinate point in a graph as illustrated in (b) of FIG. 10.

In view of the circumstances, in a case where a quadratic coefficient, calculated by the function specifying section 43, is negative, the output information generating section 44 can generate output information in accordance with the actual number of holes in a given binarized image.

Specifically, the Betti number calculating section 42 calculates a one-dimensional Betti number of each of a plurality of binarized images generated with use of respective binarization reference values which have been obtained by multiplying a standard pixel value, corresponding to B, by values which are differed from 0.55 to 0.72. Next, the function specifying section 43 calculates a plurality of coefficients, including a quadratic coefficient, which are included in a quadratic approximate expression that indicates a relationship between (i) the respective binarization reference values and (ii) the respective numbers of holes. In a case where the quadratic coefficient is positive, the output information generating section 44 can make a comparison between the actual number of holes and a predetermined discrimination reference value, and generate, based on such a comparison, a determination-purpose image (output information), as described above, in accordance with which a degree of differentiation of a cancer is discriminated.

In a case where, for example, the quadratic coefficient of the quadratic approximate expression is negative, the actual number of holes is focused on, which actual number is indicated by a binarized image generated with use of a binarization reference value that has been obtained by multiplying the standard pixel value by 0.72. For example, in a case of a normal tissue which does not include any cancer, the average number of holes was 1035. In a case of an adenoma, the average number of holes was increased to 3550. In a case of a well differentiated cancer, the average number of holes was increased to 6255. A difference in the actual number of holes between the normal tissue, the adenoma, and the well differentiated cancer was statistically significant.

This demonstrates that, in a case where a quadratic coefficient of an approximate expression is negative, it is possible to provide, based on the actual number of holes in a binarized image, information useful in discriminating a degree of differentiation of a cancer.

Embodiment 2

(Configuration of Image Analyzing Device 1a)

Next, a configuration of an image analyzing device 1a will be described below with reference to FIG. 12. FIG. 12 is a block diagram illustrating an example configuration of an image analyzing device 1a in accordance with Embodiment 2 of the present invention. The image analyzing device 1a is different from the image analyzing device 1 in that the image analyzing device 1a includes an analysis result transmitting section 9 (transmitting section), instead of a display control section 5. The analysis result transmitting section 9 obtains, from an output information generating section 44, a result of an analysis of a captured image indicated by image data which is received from an external device 8, and transmits the result to a presenting device 10.

Note that the image analyzing device 1a can include (i) a plurality of external devices 8 instead of a single external device 8 and (ii) a plurality of presenting devices 10 instead of a single presenting device 10.

(Image Analyzing System)

The following description will discuss, with reference to FIG. 13, example configurations of image analyzing systems 100 and 100a each including an image analyzing device 1a. FIG. 13 is a view schematically illustrating example configurations of image analyzing systems 100 and 100a each including an image analyzing device 1a in accordance with Embodiment 2 of the present invention. (a) of FIG. 13 illustrates an example in which an external device 8 is provided separately from a presenting device 10. (b) of FIG. 13 illustrates an example in which a presenting device 10 is connected to an external device 8a.

The image analyzing system 100 includes the external device 8, the image analyzing device 1a, and the presenting device 10. The external device 8, the image analyzing device 1a, and the presenting device 10 are each connected to an information communication network 50 such as the Internet. This allows the external device 8, the image analyzing device 1a, and the presenting device 10 to transmit/receive data to/from each other.

The external device 8 can be a device, such as a microscope, which has a function of capturing a tissue or can be alternatively a server (such as an electronic medical record server and a microscope image data server) which integrally manages images in each of which a tissue is captured.

The presenting device 10 is not limited to a specific one, provided that the presenting device 10 is a device which has a function of presenting, to a user, a result of an analysis of an image. The presenting device 10 can be, for example, a display device which includes a display. Alternatively, the presenting device 10 can be communication terminal equipment, such as a tablet terminal, which a medical worker brings with him/her.

Image data, which corresponds to a captured image obtained by capturing a tissue, is transmitted from the external device 8 to the image analyzing device 1a. Upon receipt of the image data, (i) an image analyzing section 4 analyzes the captured image, (ii) an output information generating section 44 generates output information, and (iii) the analysis result transmitting section 9 transmits the output information to the presenting device 10 or the external device 8.

The image analyzing system 100a includes the external device 8a, the image analyzing device 1a, and the presenting device 10. The external device 8a and the image analyzing device 1a are each connected to an information communication network 50 such as the Internet. This allows the external device 8a and the image analyzing device 1a to transmit/receive data to/from each other. The presenting device 10 is connected to the external device 8a.

That is, the image analyzing device 1*a* is capable of (i) receiving, from the external device 8, an image captured at a distant place, (ii) analyzing the image, and then (iii) transmitting, to the presenting device 10 and the presenting device 10*a*, at least one of output information and a determination-purpose image each of which indicates a result of an analysis. The presenting devices 10 and 10*a* can be each a device which is connected to the external device 8 or can be alternatively a device which is independent from the image analyzing device 1*a* and the external device 8.

Embodiment 3

The present invention is not limited to determination of a cancer in a tissue of a living body, and is applicable to an analysis of composition of another structure. In Embodiment 3, with reference to FIGS. 14 through 17, an example will be described in which composition of a silicone gel (structure) is analyzed.

(Composition and Image of Silicone Gel)

A silicone gel is an amorphous material which contains, as constituents, silicon atoms (Si) and oxygen atoms (O). It is known that a pattern (composition) of a bond (relationship) between molecules of the silicone gel varies between (i) a case where gelation is carried out under an acidic condition and (ii) a case where gelation is carried out under a basic condition. The following description will discuss an example of a result obtained in a case where the bond between the molecules of the silicone gel is analyzed by an image analyzing device 1, 1*a* in accordance with Embodiment 3 of the present invention.

The following description will first discuss a difference in molecular structure (bonding pattern between the molecules constituting the silicone gel) which depends on a condition under which the gelation is carried out. (a) of FIG. 14 is a view illustrating a molecular structure of a silicone gel which is obtained by carrying out gelation under an acidic condition. (b) of FIG. 14 is an image (structure image, captured image) which is obtained by capturing, with use of a transmission electron microscope, the silicone gel that is obtained by carrying out the gelation under the acidic condition. (c) of FIG. 14 is a view illustrating a molecular structure of a silicone gel which is obtained by carrying out gelation under an basic condition. (d) of FIG. 14 is an image (structure image, captured image) which is obtained by capturing, with use of a transmission electron microscope, the silicone gel that is obtained by carrying out the gelation under the basic condition. Note, in each of (b) and (d) of FIG. 14, that a whitely displayed part of the image indicates a part in which an oxygen atom is present. Note also that a scale bar indicative of 1 (one) nm is shown in the image illustrated in each of (b) and (d) of FIG. 15. A magnification at which a structure to be analyzed is captured can be set as appropriate by a person skilled in the art, based on the structure.

An image obtaining section 2 obtains, from an external device 8 such as a transmission electron microscope, the image which is obtained by capturing the silicone gel. The image thus obtained is stored in a storage section 3.

(Binarization of Image Obtained by Capturing Silicone Gel)

A binarizing section 41 first reads out the image, illustrated in (b) of FIG. 15, from the storage section 3, and then generates binarized images by binarizing the image while making binarization reference values differ from each other. FIG. 15 illustrates binarized images which are generated by binarizing the image, illustrated in (b) of FIG. 14, while making binarization reference values differ from each other. FIG. 16 illustrates binarized images which are generated by binarizing the image, illustrated in (d) of FIG. 14, while making binarization reference values differ from each other.

Note, here, that, unlike Embodiments 1 and 2, the image of the silicone gel does not include any color component such as RGB. Therefore, in Embodiment 3, the binarizing section 41 determines given pixel values as the binarization reference values.

FIGS. 15 and 16 each illustrate the binarized images which are generated in a case where (a) 200, (b) 175, (c) 150, (d) 125, (e) 100, (f) 75, and (g) 50 are set as the respective binarization reference values.

Out of the binarized images illustrated in each of FIGS. 15 and 16, a binarized image illustrated in (a) is obtained because an excessively great binarization reference value is employed. In contrast, and a binarized image illustrated in each of (f) and (g) is obtained because an excessively small binarization reference value is employed.

(Calculation of the Number of Holes in Binarized Image of Silicone Gel)

In Embodiment 3, a Betti number calculating section 42 calculates the numbers of holes (the numbers of hole-shaped regions) from the respective binarized images (b) through (e) illustrated in each of FIGS. 15 and 16. Note that a whitely displayed part of the image illustrated in each of (b) and (d) of FIG. 14 indicates a part in which an oxygen atom is present. It can be therefore said that calculating the number of holes from a binarized image is equivalent to (i) a process of counting the number of oxygen atoms present within a region included in the binarized image or (ii) a process of checking how much oxygen atoms are statistically distributed in the region included in the binarized image.

The numbers of holes thus calculated from (b), (c), (d), and (e) of FIG. 15 are 59, 45, 38, and 29, respectively. The numbers of holes thus calculated from (b), (c), (d), and (e) of FIG. 16 are 162, 137, 52, and 6, respectively.

(Specifying Function which Approximates Change in Number of Holes in Response to Change in Binarization Reference Value)

Next, a function specifying section 43 calculates a numerical value which represents a characteristic of a function that approximately indicates a change in number of holes in response to a change in binarization reference value. FIG. 17 is a graph illustrating an example of a result of analyzing composition of the silicone gel. Specifically, FIG. 17 is a graph obtained by plotting the numbers of holes along a vertical axis and plotting the binarization reference values along a horizontal axis.

In regard to (b) through (e) of each of FIGS. 15 and 16, it was possible to approximate, with use of a linear function (dotted line in FIG. 17) as an approximate expression (approximate function), the change in number of holes in response to the change in binarization reference value (see FIG. 17). Hereinafter, in FIG. 17, (i) a plot indicative of data corresponding to (b) through (e) of FIG. 15 will be referred to as data L, and (ii) a plot indicative of data corresponding to (b) through (e) of FIG. 16 will be referred to as data K. This demonstrates that each of the silicone gel which is obtained by carrying out the gelation under the acidic condition and the silicone gel which is obtained by carrying out the gelation under the basic condition contains the oxygen atoms at a corresponding given proportion. Note that each correlation coefficient ($R^2$) indicative of a degree of approximation was higher than 0.98, and this demonstrated that the approximation was considerably accurate.

The function specifying section 43 calculates (i) a linear coefficient (characteristic numerical value) of the linear function which approximately indicates the data L and (ii) a linear coefficient (characteristic numerical value) of the linear function which approximately indicates the data K. Note that the function specifying section 43 can calculate a value (characteristic numerical value) of a constant term in addition to a coefficient of a linear term of the linear function.

The linear coefficient (characteristic numerical value), which the function specifying section 43 specified and which indicates a characteristic of the linear function, was apparently different depending on whether the silicone gel was obtained by carrying out the gelation under the acidic condition or by carrying out the gelation under the basic condition.

(Determination of Silicone Gel)

This demonstrates that it is possible to discriminate a pattern (composition) of a bond between molecules of the silicone gel in accordance with the linear coefficient indicative of the characteristic of the linear function, which linear coefficient has been determined by the function specifying section 43.

An output information generating section 44 then generates output information indicative of a result of determination made on the basis of the linear coefficient indicative of the characteristic of the linear function, which linear coefficient has been specified by the function specifying section 43. This allows a user to discriminate a molecular structure of the silicone gel in accordance with the output information displayed on a screen of a display device 6.

Embodiment 3 thus illustrates by the example in which the molecular structure of the silicone gel is discriminated. Note, however, that Embodiment 3 is not limited to such an example. It is possible to assess, with high accuracy, a connection (relationship) between a plurality of constituents of any structure, with use of the image analyzing device 1, 1*a* in accordance with Embodiment 3 of the present invention.

[Software Implementation Example]

Control block (particularly, the binarizing section 41, the Betti number calculating section 42, the function specifying section 43, and the output information generating section 44) of the image analyzing device 1, 1*a* can be realized by a logic circuit (hardware) provided in an integrated circuit (IC chip) or the like or can be alternatively realized by software as executed by a central processing unit (CPU).

In the latter case, the image analyzing device 1, 1*a* includes: a CPU which executes instructions of a program that is software realizing the foregoing functions; a read only memory (ROM) or a storage device (each referred to as "storage medium") in which the program and various kinds of data are stored so as to be readable by a computer (or a CPU); and a random access memory (RAM) in which the program is loaded. An object of the present invention can be achieved by a computer (or a CPU) reading and executing the program stored in the storage medium. Examples of the storage medium encompass "a non-transitory tangible medium" such as a tape, a disk, a card, a semiconductor memory, and a programmable logic circuit. The program can be supplied to the computer via any transmission medium (such as a communication network or a broadcast wave) which allows the program to be transmitted. Note that the present invention can also be achieved in the form of a computer data signal in which the program is embodied via electronic transmission and which is embedded in a carrier wave.

The present invention is not limited to the embodiments, but can be altered by a skilled person in the art within the scope of the claims. The present invention also encompasses, in its technical scope, any embodiment derived by combining technical means disclosed in differing embodiments.

[Recap]

An image analyzing device 1, 1*a* in accordance with Aspect 1 of the present invention includes: a binarizing section 41 configured to generate a plurality of binarized images by binarizing, a plurality of times, a single captured image, which is obtained by capturing a structure, while making binarization reference values differ from each other; a space number calculating section (Betti number calculating section 42) configured to calculate the numbers of hole-shaped regions from the respective plurality of binarized images generated by the binarizing section; a specifying section (function specifying section 43) configured to specify a characteristic numerical value that characterizes a correspondence between (i) the respective binarization reference values and (ii) the respective numbers of hole-shaped regions; and an output information generating section 44 configured to generate output information corresponding to the characteristic numerical value specified by the specifying section.

According to the above configuration, the image analyzing device calculates the numbers of hole-shaped regions from respective plurality of binarized images generated by binarizing, a plurality of times, a single captured image, which is obtained by capturing a structure, while making binarization reference values differ from each other. Note, here, that a hole-shaped region indicates a space (hole) shown in a captured image which is a two-dimensional surface. As a process of calculating the numbers of hole-shaped regions, a process of calculating one-dimensional Betti numbers from the respective plurality of binarized images can be carried out. Note that a program for calculating a Betti number from an image is publicly known, and a device which carries out the program can be used as the space number calculating section.

Next, that image analyzing device determines a characteristic numerical value that characterizes a correspondence between (i) the respective binarization reference values and (ii) the respective numbers of hole-shaped regions. The image analyzing device then generates output information corresponding to the characteristic numerical value. Note that the image analyzing device can determine at least one characteristic numerical value.

Therefore, it is possible to generate, as output information, information which mathematically indicates a relationship between constituents, and possible to determine composition of each of various structures. Note that, as used herein, a "structure" means a unit in which constituents of one or more kinds aggregate in a given pattern, and can be a tissue of a living body which tissue is made of an aggregate of cells and the like, a mineral structure which is made of an aggregate of crystal grains, a structure of which a resin product is made and which is made of an aggregate of molecules of a resin material such as a silicone, or the like.

For example, it is assumed that a degree of differentiation of a cancer occurring in a tissue of a living body is discriminated. In this case, since a relationship (strength of a connection) between constituents of the tissue of the living body varies, it is possible to extract information useful in discriminating the degree of differentiation of the cancer, by converting the relationship between the constituents into a numerical value.

The image analyzing device in accordance with Aspect 2 of the present invention can be arranged such that, in Aspect 1, the specifying section specifies at least one of a plurality of characteristic numerical values which represent a characteristic of a function that approximately indicates the correspondence between (i) the respective binarization reference values and (ii) the respective numbers of hole-shaped regions.

That is, the image analyzing device in accordance with Aspect 2 can include: a binarizing section 41 configured to generate a plurality of binarized images by binarizing, a plurality of times, a single captured image which is obtained by capturing a structure, while making binarization reference values differ from each other; a space number calculating section (Betti number calculating section 42) configured to calculate the numbers of hole-shaped regions from the respective plurality of binarized images generated by the binarizing section; a function specifying section 43 configured to specify a plurality of characteristic numerical values which represent a characteristic of a function that approximately indicates a correspondence between (i) the respective binarization reference values and (ii) the respective numbers of hole-shaped regions; and an output information generating section 44 configured to generate output information corresponding to at least one of the plurality of characteristic numerical values specified by the specifying section.

This makes it possible to use the plurality of characteristic numerical values which represent the characteristic of the function that approximately indicates the correspondence between (i) the respective binarization reference values and (ii) the respective numbers of hole-shaped regions, as a plurality of characteristic numerical values which characterize the correspondence between (i) the respective binarization reference values and (ii) the respective numbers of hole-shaped regions.

The image analyzing device in accordance with Aspect 3 of the present invention can be arranged such that, in Aspect 1 or 2, the output information generating section generates output information corresponding to a position of a point (coordinate point), which has, as coordinates, a plurality of characteristic numerical values specified by the specifying section, in a coordinate space defined by a plurality of coordinate axes which correspond to the respective plurality of characteristic numerical values.

This makes it possible to output information useful in assessing, with high accuracy, a relationship between constituents of a structure.

The inventors of the present invention has found that, in a case where a tissue of a living body is to be analyzed, it is likely to be possible to discriminate a degree of differentiation of a cancer in the tissue of the living body, by a position of a coordinate point in a coordinate space.

By thus configuring the image analyzing device, it is possible to generate output information corresponding to a position of a coordinate point, and possible to appropriately assist a pathologist in discriminating a degree of differentiation of a cancer, by presenting the output information to the pathologist.

The image analyzing device in accordance with Aspect 4 of the present invention can be arranged so as to, in any one of Aspects 1 through 3, further include a dividing section (binarizing section 41) configured to divide the single captured image into a plurality of divided regions each having a given size, the space number calculating section calculating the numbers of hole-shaped regions for each of the plurality of divided regions generated by the dividing section, the specifying section specifying a plurality of characteristic numerical values for the each of the plurality of divided regions, the output information generating section generating the output information for the each of the plurality of divided regions.

According to the above configuration, the dividing section divides a captured image, which is obtained by capturing a structure, into divided regions each having a given size, and the space number calculating section calculates the numbers of hole-shaped regions for each of the divided regions generated by the dividing section. The specifying section specifies, for each of the divided regions, a plurality of characteristic numerical values which represent a characteristic of a function, in accordance with the numbers of hole-shaped regions which the space number calculating section has calculated for each of the divided regions. The output information generating section then generates output information corresponding to a position of a point having, as coordinates, the plurality of characteristic numerical values determined for each of the divided regions.

Therefore, it is possible to increase accuracy with which a relationship between constituents of a structure is converted into a numerical value, as compared with a case where an entire captured image, which is obtained by capturing the structure, is analyzed. Furthermore, it is possible to determine which divided region in the captured image is a target region.

The image analyzing device in accordance with Aspect 5 of the present invention can be arranged such that, in Aspect 4, the output information generating section generates, as the output information, a determination-purpose image including the plurality of divided regions, the output information generating section generating the determination-purpose image so that the each of the plurality of divided regions is presented, in the determination-purpose image, in a manner corresponding to the plurality of characteristic numerical values specified for the each of the plurality of divided regions of the single captured image.

This makes it possible to present, to a user, an intuitive and greatly convenient determination-purpose image which includes information necessary to determine composition of a structure.

The image analyzing device in accordance with Aspect 6 of the present invention can be arranged such that, in any one of Aspects 1 through 5, the binarizing section determines the binarization reference values in accordance with pixel values of respective pixels for the single captured image.

This makes it possible to determine binarization reference values used to generate respective binarized images, in accordance with pixel values that allows a relationship between constituents of a tissue, captured in a captured image, to be more clearly specified.

Note that, in a case of a tissue of a living body, the tissue is stained, sectioned, and then captured in many cases. Depending on a pigment used to stain the tissue, it is possible to appropriately determine binarization reference values used to generate respective binarized images. In this case, out of pixel values corresponding to a given color (for example, blue (B)) constituting a captured image, a pixel value which is the highest in frequency of appearance can be determined as a standard pixel value, and then the binarization reference values can be determined in accordance with the standard pixel value.

The image analyzing device in accordance with Aspect 7 of the present invention can be arranged such that, in any one of Aspects 1 through 6, the specifying section specifies a plurality of coefficients, including an n-th degree coefficient, of an n-th degree expression (n is equal to or greater than 1)

which indicates the correspondence between (i) the respective binarization reference values and (ii) the respective numbers of hole-shaped regions.

In a case where points each having, as coordinates, a binarization reference value and the number of hole-shaped regions are plotted in a graph, it is possible to approximate, with use of an n-th degree function, a change in number of hole-shaped regions in response to a change in binarization reference value. That is, in many cases, it is possible to approximate, with use of an n-th degree function, a correspondence between (i) respective binarization reference values and (ii) the respective numbers of hole-shaped regions.

According to the above configuration, a plurality of coefficients, including a coefficient of an n-th degree expression, are determined. This makes it possible to extract the correspondence between (i) the respective binarization reference values and (ii) the respective numbers of hole-shaped regions, in accordance with an objective and simple mathematical process. In this case, it is possible to regard the plurality of coefficients as a plurality of characteristic numerical values which represent a characteristic of a function.

An image analyzing system in accordance with Aspect 8 of the present invention includes: an image analyzing device recited in any one of Aspects 1 through 7; an external device configured to transmit, to the image analyzing device, image data indicative of a captured image; and a presenting device configured to (a) obtain output information generated by the image analyzing device and (b) present the output information.

This makes it possible to receive a captured image which is captured with use of the external device at a distant place, analyze the captured image, and present the captured image and output information to a user at a distant place.

In order to attain the above object, an image analyzing method in accordance with Aspect 9 of the present invention is an image analyzing method for use in an image analyzing device 1, 1a that analyzes a single captured image which is obtained by capturing a structure, the method including the steps of: (a) generating a plurality of binarized images by binarizing, a plurality of times, the single captured image while making binarization reference values differ from each other (S2); (b) calculating the numbers of hole-shaped regions from the respective plurality of binarized images generated in the step (a) (S3); (c) specifying a characteristic numerical value that characterizes a correspondence between (i) the respective binarization reference values and (ii) the respective numbers of hole-shaped regions (S4); and (d) generating output information corresponding to the characteristic numerical value specified in the step (c) (S5). According to the above configuration, it is possible to bring about an effect similar to that brought about by Aspect 1.

The technical scope of the present invention also encompasses (i) an image analyzing program for causing a computer to function as an image analyzing device, the image analyzing program causing the computer to function as each section, and (ii) a recording medium in which the image analyzing program is computer-readably recorded.

REFERENCE SIGNS LIST 1, 1a Image analyzing device
2 Image obtaining section (receiving section)
4 Image analyzing section (image analyzing device)
5 Display control section
6 Display device (presenting section)
8 External device
9 Analysis result transmitting section (transmitting section)
10 Presenting device
41 Binarizing section (dividing section)
42 Betti number calculating section (space number calculating section)
43 Function specifying section (specifying section)
44 Output information generating section
100, 100a Image analyzing system
S2 Binarizing step
S3 Space number calculating step
S4 Determining step
S5 Output information generating step

The invention claimed is:

1. An image analyzing device comprising:
a binarizing section configured to generate a plurality of binarized images by binarizing, a plurality of times, a single captured image, which is obtained by capturing a structure, while making binarization reference values differ from each other;
a space number calculating section configured to calculate the numbers of hole-shaped regions from the respective plurality of binarized images generated by the binarizing section;
a specifying section configured to specify a characteristic numerical value that characterizes a correspondence between (i) the respective binarization reference values and (ii) the respective numbers of hole-shaped regions; and
an output information generating section configured to generate output information corresponding to the characteristic numerical value specified by the specifying section.

2. The image analyzing device as set forth in claim 1, wherein the specifying section specifies at least one of a plurality of characteristic numerical values which represent a characteristic of a function that approximately indicates the correspondence between (i) the respective binarization reference values and (ii) the respective numbers of hole-shaped regions.

3. The image analyzing device as set forth in claim 1, wherein the output information generating section generates output information corresponding to a position of a point, which has, as coordinates, a plurality of characteristic numerical values calculated by the specifying section, in a coordinate space defined by a plurality of coordinate axes which correspond to the respective plurality of characteristic numerical values.

4. An image analyzing device as set forth in claim 1, further comprising a dividing section configured to divide the single captured image into a plurality of divided regions each having a given size,
the space number calculating section calculating the numbers of hole-shaped regions for each of the plurality of divided regions generated by the dividing section,
the specifying section calculating a plurality of characteristic numerical values for the each of the plurality of divided regions,
the output information generating section generating the output information for the each of the plurality of divided regions.

5. The image analyzing device as set forth in claim 4, wherein the output information generating section generates, as the output information, a determination-purpose image including the plurality of divided regions,
the output information generating section generating the determination-purpose image so that the each of the plurality of divided regions is presented, in the determination-purpose image, in a manner corresponding to the plurality of characteristic numerical values specified for the each of the plurality of divided regions of the single captured image.

6. The image analyzing device as set forth in claim 1, wherein the binarizing section determines the binarization reference values in accordance with pixel values of respective pixels for the single captured image.

7. The image analyzing device as set forth in claim 1, wherein the specifying section calculates a plurality of coefficients, including an n-th degree coefficient, of an n-th degree expression (n is equal to or greater than 1) which indicates the correspondence between (i) the respective binarization reference values and (ii) the respective numbers of hole-shaped regions.

8. An image analyzing system comprising: an image analyzing device recited in claim 1;

an external device configured to transmit, to the image analyzing device, image data indicative of a captured image; and a presenting device configured to (a) obtain output information generated by the image analyzing device and (b) present the output information.

9. An image analyzing method for use in an image analyzing device that analyzes a single captured image which is obtained by capturing a structure, said method comprising the steps of:
(a) generating a plurality of binarized images by binarizing, a plurality of times, the single captured image while making binarization reference values differ from each other;
(b) calculating the numbers of hole-shaped regions from the respective plurality of binarized images generated in the step (a);
(c) specifying a characteristic numerical value that characterizes a correspondence between (i) the respective binarization reference values and (ii) the respective numbers of hole-shaped regions; and
(d) generating output information corresponding to the characteristic numerical value specified in the step (c).

10. A computer-readable non-transitory recording medium in which an image analyzing program for causing a computer to function as an image analyzing device recited in claim 1 is computer-readably recorded, said image analyzing program causing the computer to function as a binarizing section, a space number calculating section, a specifying section, and an output information generating section.

* * * * *